US008533746B2

(12) United States Patent
Nolan et al.

(10) Patent No.: US 8,533,746 B2
(45) Date of Patent: Sep. 10, 2013

(54) HEALTH INTEGRATION PLATFORM API

(75) Inventors: Sean Patrick Nolan, Bellevue, WA (US); Jeffrey Dick Jones, Woodinville, WA (US); Johnson T. Apacible, Mercer Island, WA (US); Vijay Varadan, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 1164 days.

(21) Appl. No.: 11/745,902

(22) Filed: May 8, 2007

(65) Prior Publication Data

US 2008/0104615 A1 May 1, 2008

Related U.S. Application Data

(60) Provisional application No. 60/863,897, filed on Nov. 1, 2006.

(51) Int. Cl.
| G06F 9/44 | (2006.01) |
| G06F 7/04 | (2006.01) |
| G06F 7/00 | (2006.01) |
| G06Q 50/00 | (2012.01) |

(52) U.S. Cl.
USPC ............ 719/328; 726/2; 726/4; 726/5; 705/2; 705/3; 707/705

(58) Field of Classification Search
None
See application file for complete search history.

(56) References Cited

U.S. PATENT DOCUMENTS

| 5,213,555 A | 5/1993 | Hood et al. |
| 5,265,010 A | 11/1993 | Evans-Paganelli et al. |
| 5,690,582 A | 11/1997 | Ulrich et al. |
| 5,857,967 A | 1/1999 | Frid et al. |
| 5,890,995 A | 4/1999 | Bobick et al. |
| 5,924,074 A | 7/1999 | Evans |
| 6,002,982 A | 12/1999 | Fry |
| 6,013,007 A | 1/2000 | Root et al. |
| 6,057,758 A | 5/2000 | Dempsey et al. |
| 6,151,624 A | 11/2000 | Teare et al. |
| 6,253,208 B1 | 6/2001 | Wittgreffe et al. |
| 6,259,944 B1 | 7/2001 | Margulis et al. |

(Continued)

FOREIGN PATENT DOCUMENTS

| JP | 2004-164052 A | 6/2004 |
| JP | 2005-165442 A | 6/2005 |

(Continued)

OTHER PUBLICATIONS

International Search Report for PCT Application No. PCT / US 2007/ 08335, mailed Apr. 21, 2008, 4 pages.

(Continued)

*Primary Examiner* — Qing Wu
(74) *Attorney, Agent, or Firm* — Hope Balduff, LLC

(57) ABSTRACT

An application program interface (API) is provided for requesting, storing, and otherwise accessing data within a health integration network. The API facilitates secure and seamless access to the centrally-stored data by offering authentication/authorization, as well as the ability to receive requests in an extensible language format, such as XML, and returns resulting data in XML format. The data can also have transformation, style and/or schema information associated with it which can be returned in the resulting XML and/or applied to the data beforehand by the API. The API can be utilized in many environment architectures including XML over HTTP and a software development kit (SDK).

21 Claims, 11 Drawing Sheets

(56) References Cited

U.S. PATENT DOCUMENTS

| | | | |
|---|---|---|---|
| 6,374,237 B1 | 4/2002 | Reese | |
| 6,542,902 B2 | 4/2003 | Dulong et al. | |
| 6,578,068 B1 | 6/2003 | Bowman-Amuah | |
| 6,622,231 B2 | 9/2003 | Kaufman et al. | |
| 6,692,435 B1 | 2/2004 | Choate | |
| 6,704,798 B1 | 3/2004 | Mogul | |
| 6,763,382 B1 | 7/2004 | Balakrishnan et al. | |
| 6,912,534 B2 | 6/2005 | DeBettencourt et al. | |
| 6,996,558 B2* | 2/2006 | Dettinger et al. | 1/1 |
| 7,031,954 B1 | 4/2006 | Kirsch | |
| 7,082,427 B1 | 7/2006 | Selbel et al. | |
| 7,111,172 B1 | 9/2006 | Duane et al. | |
| 7,203,623 B2 | 4/2007 | Garcea et al. | |
| 7,217,224 B2 | 5/2007 | Thomas | |
| 7,230,529 B2 | 6/2007 | Ketcherside, Jr. et al. | |
| 7,292,867 B2 | 11/2007 | Werner et al. | |
| 7,317,927 B2 | 1/2008 | Staton et al. | |
| 7,363,298 B2* | 4/2008 | Kadatch et al. | 1/1 |
| 7,398,263 B2* | 7/2008 | Dettinger et al. | 1/1 |
| 7,480,512 B2 | 1/2009 | Graham et al. | |
| 7,603,255 B2 | 10/2009 | Case et al. | |
| 7,613,722 B2 | 11/2009 | Horvitz et al. | |
| 7,695,406 B2 | 4/2010 | Waters | |
| 7,702,906 B1 | 4/2010 | Karr et al. | |
| 7,730,528 B2* | 6/2010 | Chun et al. | 726/12 |
| 7,822,620 B2 | 10/2010 | Dixon et al. | |
| 7,904,487 B2 | 3/2011 | Ghatare | |
| 2001/0000358 A1 | 4/2001 | Isomichi et al. | |
| 2001/0001147 A1 | 5/2001 | Hutchison et al. | |
| 2001/0009454 A1 | 7/2001 | Manico et al. | |
| 2002/0010679 A1 | 1/2002 | Felsher | |
| 2002/0103811 A1 | 8/2002 | Fankhauser et al. | |
| 2002/0120472 A1 | 8/2002 | Dvorak et al. | |
| 2002/0126849 A1 | 9/2002 | Howard et al. | |
| 2002/0129031 A1 | 9/2002 | Lau et al. | |
| 2002/0138324 A1 | 9/2002 | Zarefoss et al. | |
| 2002/0198739 A1 | 12/2002 | Lau et al. | |
| 2003/0035371 A1 | 2/2003 | Reed et al. | |
| 2003/0037054 A1 | 2/2003 | Dutta et al. | |
| 2003/0037069 A1 | 2/2003 | Davison | |
| 2003/0051146 A1 | 3/2003 | Ebina et al. | |
| 2003/0078934 A1 | 4/2003 | Cappellucci et al. | |
| 2003/0081791 A1 | 5/2003 | Erickson et al. | |
| 2003/0088438 A1 | 5/2003 | Maughan et al. | |
| 2003/0149526 A1 | 8/2003 | Zhou et al. | |
| 2003/0154406 A1 | 8/2003 | Honarvar et al. | |
| 2003/0167274 A1* | 9/2003 | Dettinger et al. | 707/100 |
| 2003/0167456 A1 | 9/2003 | Sabharwal | |
| 2003/0182361 A1 | 9/2003 | Jensen et al. | |
| 2003/0212673 A1 | 11/2003 | Kadayam et al. | |
| 2004/0017917 A1 | 1/2004 | Hammersmith et al. | |
| 2004/0064502 A1 | 4/2004 | Yellepeddy et al. | |
| 2004/0068653 A1 | 4/2004 | Fascenda | |
| 2004/0088374 A1 | 5/2004 | Webb et al. | |
| 2004/0088548 A1 | 5/2004 | Smetters et al. | |
| 2004/0148276 A1* | 7/2004 | Dettinger et al. | 707/3 |
| 2004/0228492 A1 | 11/2004 | Park | |
| 2005/0075996 A1* | 4/2005 | Dettinger et al. | 707/1 |
| 2005/0081039 A1 | 4/2005 | Lee et al. | |
| 2005/0108537 A1 | 5/2005 | Puri et al. | |
| 2005/0114501 A1 | 5/2005 | Raden et al. | |
| 2005/0138417 A1 | 6/2005 | McNerney et al. | |
| 2005/0144182 A1* | 6/2005 | Boris et al. | 707/100 |
| 2005/0165798 A1 | 7/2005 | Cherkauer et al. | |
| 2005/0177749 A1 | 8/2005 | Ovadia | |
| 2005/0197859 A1 | 9/2005 | Wilson et al. | |
| 2005/0203771 A1 | 9/2005 | Achan | |
| 2005/0210005 A1 | 9/2005 | Thompson et al. | |
| 2005/0228808 A1 | 10/2005 | Mamou et al. | |
| 2005/0239601 A1 | 10/2005 | Thomas | |
| 2005/0251533 A1 | 11/2005 | Harken | |
| 2005/0256834 A1 | 11/2005 | Millington et al. | |
| 2005/0273365 A1 | 12/2005 | Baumgartner et al. | |
| 2006/0004588 A1 | 1/2006 | Ananda | |
| 2006/0005244 A1 | 1/2006 | Garbow et al. | |
| 2006/0010127 A1* | 1/2006 | Dettinger et al. | 707/4 |
| 2006/0020506 A1 | 1/2006 | Axe et al. | |
| 2006/0020581 A1 | 1/2006 | Dettinger et al. | |
| 2006/0031094 A1 | 2/2006 | Cohen et al. | |
| 2006/0089123 A1 | 4/2006 | Frank | |
| 2006/0129540 A1 | 6/2006 | Hillis et al. | |
| 2006/0150086 A1 | 7/2006 | Griffin et al. | |
| 2006/0155584 A1 | 7/2006 | Aggarwal | |
| 2006/0172724 A1 | 8/2006 | Linkert et al. | |
| 2006/0178908 A1 | 8/2006 | Rappaport | |
| 2006/0179003 A1 | 8/2006 | Steele et al. | |
| 2006/0179178 A1 | 8/2006 | King | |
| 2006/0206877 A1 | 9/2006 | Kohlmeier et al. | |
| 2006/0229918 A1 | 10/2006 | Fotsch et al. | |
| 2006/0277198 A1 | 12/2006 | Error et al. | |
| 2006/0277215 A1 | 12/2006 | Siegel | |
| 2007/0015532 A1 | 1/2007 | Deelman | |
| 2007/0027961 A1 | 2/2007 | Holzer | |
| 2007/0055552 A1 | 3/2007 | St. Clair et al. | |
| 2007/0061318 A1 | 3/2007 | Azizi et al. | |
| 2007/0073664 A1 | 3/2007 | Ahn | |
| 2007/0073829 A1 | 3/2007 | Volodarsky et al. | |
| 2007/0078686 A1 | 4/2007 | Dettinger et al. | |
| 2007/0079332 A1 | 4/2007 | McEnroe | |
| 2007/0083393 A1 | 4/2007 | Howell | |
| 2007/0118540 A1 | 5/2007 | Guo | |
| 2007/0130044 A1 | 6/2007 | Rowan | |
| 2007/0143273 A1 | 6/2007 | Knaus et al. | |
| 2007/0143342 A1 | 6/2007 | VanNostrand | |
| 2007/0156655 A1 | 7/2007 | Butler et al. | |
| 2007/0156842 A1 | 7/2007 | Vermeulen et al. | |
| 2007/0157225 A1 | 7/2007 | Harada et al. | |
| 2007/0208746 A1 | 9/2007 | Koide et al. | |
| 2007/0214015 A1 | 9/2007 | Christian | |
| 2007/0220009 A1 | 9/2007 | Morris et al. | |
| 2007/0237179 A1 | 10/2007 | Sethi | |
| 2007/0239890 A1 | 10/2007 | Chen et al. | |
| 2007/0266185 A1 | 11/2007 | Goddi et al. | |
| 2007/0277228 A1 | 11/2007 | Curtis et al. | |
| 2008/0033736 A1 | 2/2008 | Bulman | |
| 2008/0101374 A1 | 5/2008 | West | |
| 2008/0101597 A1 | 5/2008 | Nolan et al. | |
| 2008/0103794 A1 | 5/2008 | Pettiross et al. | |
| 2008/0103818 A1 | 5/2008 | Nolan et al. | |
| 2008/0103830 A1 | 5/2008 | Apacible et al. | |
| 2008/0104012 A1 | 5/2008 | Nolan et al. | |
| 2008/0104104 A1 | 5/2008 | Nolan et al. | |
| 2008/0104617 A1 | 5/2008 | Apacible et al. | |
| 2008/0109158 A1 | 5/2008 | Huhtala et al. | |
| 2008/0147790 A1 | 6/2008 | Malaney et al. | |
| 2008/0172237 A1 | 7/2008 | Lai et al. | |
| 2008/0306872 A1 | 12/2008 | Felsher | |
| 2009/0013063 A1 | 1/2009 | Soman | |
| 2009/0063665 A1 | 3/2009 | Bagepalli et al. | |
| 2009/0064287 A1 | 3/2009 | Bagepalli et al. | |
| 2009/0287837 A1 | 11/2009 | Felsher | |
| 2010/0004097 A1 | 1/2010 | D'Eredita | |
| 2010/0160014 A1 | 6/2010 | Galasso et al. | |

FOREIGN PATENT DOCUMENTS

| | | |
|---|---|---|
| KR | 10-2004-0098962 | 11/2004 |
| KR | 10-2006-0024560 | 3/2006 |
| WO | WO 98/33130 | 7/1998 |
| WO | WO 01/86424 | 11/2001 |
| WO | WO 2004/015542 | 2/2004 |
| WO | WO 2006/026673 A2 | 3/2006 |
| WO | 2008057973 | 5/2008 |

OTHER PUBLICATIONS

OA dated Jul. 21, 2011 for U.S. Appl. No. 11/860,627, 19 pages.

Seals, The use of XML in Healthcare Information Management, Summer 2000, Journal of Healthcare Information Management, 14(2): 85-95.

Holanda et al., "A Lossless Compression Method for Internet Packet Headers," 2005, Next Generation Internet Networks—IEEE, pp. 233-239.

Chinese Official Action dated Feb. 14, 2012 in Chinese Application No. 200780040929.5.

U.S. Official Action dated Aug. 5, 2010 in U.S. Appl. No. 11/745,904.
U.S. Official Action dated Jan. 24, 2011 in U.S. Appl. No. 11/745,904.
U.S. Official Action dated Aug. 8, 2011 in U.S. Appl. No. 11/745,904.
U.S. Notice of Allowance dated Feb. 17, 2012 in U.S. Appl. No. 11/745,904.
U.S. Official Action dated Aug. 5, 2010 in U.S. Appl. No. 11/745,898.
U.S. Official Action dated Dec. 23, 2010 in U.S. Appl. No. 11/745,898.
U.S. Official Action dated Mar. 17, 2011 in U.S. Appl. No. 11/745,898.
U.S. Official Action dated Aug. 18, 2011 in U.S. Appl. No. 11/745,898.
U.S. Official Action dated Dec. 8, 2011 in U.S. Appl. No. 11/745,898.
U.S. Official Action dated Sep. 18, 2009 in U.S. Appl. No. 11/759,359.
U.S. Official Action dated Apr. 14, 2010 in U.S. Appl. No. 11/759,359.
U.S. Official Action dated Aug. 4, 2010 in U.S. Appl. No. 11/759,359.
U.S. Official Action dated Jan. 20, 2011 in U.S. Appl. No. 11/759,359.
U.S. Official Action dated Nov. 10, 2011 in U.S. Appl. No. 11/759,359.
U.S. Official Action dated Jan. 6, 2011 in U.S. Appl. No. 11/759,361.
U.S. Official Action dated Jul. 8, 2011 in U.S. Appl. No. 11/759,361.
U.S. Official Action dated Apr. 1, 2010 in U.S. Appl. No. 11/760,218.
U.S. Official Action dated Aug. 13, 2010 in U.S. Appl. No. 11/760,218.
U.S. Official Action dated May 26, 2011 in U.S. Appl. No. 11/760,218.
U.S. Official Action dated Mar. 16, 2012 in U.S. Appl. No. 11/860,627.
Chinese OA, mailing date Dec. 27, 2010, for Chinese Application No. 200780040929.5, 9 pages.—Filed in IDS dated Feb. 4, 2011—refiling with full translation of CN OA.
OA dated Feb. 16, 2011 for U.S. Appl. No. 11/860,238, 22 pages.
OA dated Feb. 4, 2011 for U.S. Appl. No. 11/860,627, 22 pages.
Peng Gong, et al., An Intelligent Middleware for Dynamic Integration of Heterogeneous Health Care Applications. Http://ieeexplore.ieee.org/iel5/9520/30168/01385992.pdf?isNumber. Last accessed on Aug. 1, 2007, 8 pages.
J.A Maldonado, et al. A Mediator-Based Approach for the Integration of Distributed Electonic Healthcare Records. Http://pangea.upv.es/weblogs/pedcremo/wp-content/articles/MEDICON2004.PDF. Last acessed on Aug. 1, 2007, 4 pages.
David J. Steiner, et al. Medical Data Abstractionism : Fitting on EMR to Radically Evolving Medical Information Sytems. Http://cmbi.bjmu.edu.cn/news/report/2004/medinfo2004/pdffiles/papers/4130Steiner.pdf. Last accessed on Aug. 1, 2007, 5 pages.
OA dated Nov. 15, 2010 for U.S. Appl. No. 11/860,627, 13 pages.
OA dated May 4, 2010 for U.S. Appl. No. 11/860,627, 14 pages.
Benefiting Healthcare Delivery with Secure Data Management. Http://www.sun.com/storagetek/docs/503238_5800_Healthcare_LF.pdf. Last accessed on Aug. 1, 2007.
Integrated Health Care Information System. Apr. 2004. http://www.ericsson.com/hr/products/e-health/Technical_Description_IHCIS_R2A.pdf.
Richard J. Gallagher, et al. An Audit Server for Monitoring Usage of Clinical Information Systems http://www.amia.org/pubs/symposia/D004856.pdf. Last accessed on Aug. 1, 2007.
Daniel R. Masys, et sl., Patient-Centered Access to Secure Systems Online (PCASSO): A Secure Approach to Clinical Data Access via the World Wide Web. Http://medicine.ucsd.edu/pcasso/pubs/amia-act97.pdf. Last accessed on Aug. 1, 2007.
OA dated Nov. 9, 2010 for U.S. Appl. No. 11/860,238, 19 pages.
Chinese OA, mailing date Dec. 27, 2010, for Chinese Application No. 200780040929.5, 7 pages.
Tohru, Ishiguro, "Challenge to Grid System Using OGSA GT3; Service Oriented System by Grid," Mar. 1, 2004, Java Developer, No. 20, pp. 72-79, Softbank Publishing, Japan.
Japanese Official Action dated Jun. 8, 2012 in Japanese Application No. 2009-535477.
International Search Report dated Mar. 16, 2009 in International Application No. PCT/US08/077552.
International Search Report dated May 22, 2009 in International Application No. PCT/US08/077563.
International Search Report dated Feb. 25, 2009 in International Application No. PCT/US08/077567.
U.S. Notice of Allowance dated Jun. 19, 2012 in U.S. Appl. No. 11/745,904.
U.S. Official Action dated Mar. 30, 2012 in U.S. Appl. No. 11/745,898.
U.S. Official Action dated Jul. 19, 2012 in U.S. Appl. No. 11/759,359.
U.S. Official Action dated Oct. 29, 2010 in U.S. Appl. No. 11/860,016.
U.S. Official Action dated May 13, 2011 in U.S. Appl. No. 11/860,016.
U.S. Official Action dated Jul. 19, 2011 in U.S. Appl. No. 11/860,016.
U.S. Official Action dated Nov. 17, 2009 in U.S. Appl. No. 11/860,371.
U.S. Official Action dated Apr. 23, 2010 in U.S. Appl. No. 11/860,371.
U.S. Official Action dated Nov. 19, 2010 in U.S. Appl. No. 11/860,371.
U.S. Official Action dated Mar. 9, 2011 in U.S. Appl. No. 11/860,371.
U.S. Official Action dated Jul. 15, 2011 in U.S. Appl. No. 11/860,371.
U.S. Official Action dated Nov. 17, 2011 in U.S. Appl. No. 11/860,371.
U.S. Official Action dated Jun. 14, 2010 in U.S. Appl. No. 11/860,381.
U.S. Official Action dated Mar. 4, 2011 in U.S. Appl. No. 11/860,381.
U.S. Official Action dated Oct. 21, 2011 in U.S. Appl. No. 11/860,381.
"Design and Implementation Guidelines for Web Clients," 2003, Microsoft, retrieved Aug. 1, 2007 from http://www.willydev.net/descargas/PartnerAndPractices/WillyDev_DIGWC.pdf, 288 pages.
C. H. Crawford, et al. Toward an on Demand Service-Oriented Architecture. Aug. 2, 2007. retrieved from https://lwww.research.ibm.com/journal/sj/441/crawford.html, 24 pages.
Sriram Anand. "Managing Enterprise Data Complexity Using Web Services: Part 1," Jun. 28, 2005, retrieved from http://webservices.sys-con.com.read/104940_2.htm., 3 pages.
"Creating a Custom Data Paging Solution with IBM WebSphere Portlet Factory," Jun. 21, 2007. retrieved from http://download.boulder.ibm.com/ibmdl/pub/software/dw/wes/pdf/wpfsamps/CustomDataPaging.pdf. 5 pages.
Mudigonda et al., "Overcoming the memory wall in packet processing: Hammers or Ladders," 2005, ANC S Symposium, pp. 1-10.
U.S. Official Action dated Jan. 9, 2013 in U.S. Appl. No. 11/759,359.
U.S. Notice of Allowance dated Nov. 2, 2012 in U.S. Appl. No. 11/860,627.
U.S. Official Action dated Oct. 25, 2012 in U.S. Appl. No. 11/860,381.
European Search Report dated Nov. 20, 2012 in European Application No. 08834015.3.
European Search Report dated Apr. 17, 2013 in European Application No. 07863801.2.
U.S. Official Action dated Jun. 3, 2013 in U.S. Appl. No. 11/860,371.

* cited by examiner

HEALTH INTEGRATION PLATFORM API

CROSS-REFERENCE TO RELATED APPLICATION(S)

This application claims the benefit of U.S. Provisional Patent Application Ser. No. 60/863,897 filed on Nov. 1, 2006, entitled "INTERACTIVE AND INTUITIVE HEALTH AND FITNESS TRACKING," the entirety of which is incorporated herein by reference.

BACKGROUND

The evolution of computers and networking technologies from high-cost, low performance data processing systems to low cost, high-performance communication, problem solving, and entertainment systems has provided a cost-effective and time saving means to lessen the burden of performing every day tasks such as correspondence, bill paying, shopping, budgeting information and gathering, etc. For example, a computing system interfaced to the Internet, by way of wire or wireless technology, can provide a user with a channel for nearly instantaneous access to a wealth of information from a repository of web sites and servers located around the world. Such a system, as well, allows a user to not only gather information, but also to provide information to disparate sources. As such, online data storing and management has become increasingly popular.

For example, collaborative social networking websites have exploded world-wide. These sites allow users to create remotely stored profiles including personal data such as age, gender, schools attended, graduating class, places of employment, etc. The sites subsequently allow other users to search the foregoing criteria in an attempt to locate other users—be it to find a companion with similar interests or locate a long lost friend from high school. As another more practical example, banking websites offer users the ability to remotely store information concerning bills to be paid. By utilizing this feature, users can automatically schedule bill payments to be made from their bank account which will be automatically debited when the payment is scheduled. This allows simultaneous electronic management of account balancing and bill paying such to save the user from manually entering checks into the register of their checkbook.

Another area of great interest in this country and the entire world is personal health and fitness. Many vastly differing concerns can be discussed in this area, such as setting and obtaining personal fitness goals and the vastly disparate topic of the inefficiencies existing in our health system. For example, today an individual wishing to receive pharmaceutical treatment for illness must first see their primary care physician. Before seeing the physician, the patient will, many times, be required to show their health insurance coverage card. During the visit, the physician will typically write a prescription for the patient. The patient, then, takes the prescription to the pharmacy for fulfillment at which time they may need to furnish their health insurance coverage card again. The pharmacy fills the prescription, notifies insurance, deducts any coverage amount and transfers the prescription to the patient upon payment of the balance. These manual steps are time-consuming, annoying, and inefficient.

SUMMARY

The following presents a simplified summary in order to provide a basic understanding of some aspects described herein. This summary is not an extensive overview nor is intended to identify key/critical elements or to delineate the scope of the various aspects described herein. Its sole purpose is to present some concepts in a simplified form as a prelude to the more detailed description that is presented later.

An application program interface (API) for communicating with a health integration network is provided wherein an application can utilize the API to retrieve, store, and otherwise access or modify personal health and fitness related data. The API can communicate with the application in an extensible language format, such as extensible markup language (XML) to facilitate an open system where changes can occur to the requesting or responding XML without requiring new code to be implemented. Additionally, however, the API can require compliance with an XML schema to retain a level of common formatting necessary to keep the open system operable. The data that can be requested, stored, and returned through the API can be self-describing as well, having associated schemas, and also transformation and style information to facilitate intelligent rendering of the data. The API can also provide a layer of authentication/authorization of applications and users to access data on different levels.

The data stored in the system can be, for example, data relating to health such as blood pressure readings, insurance information, prescriptions, family history, personal medical history, diagnoses, allergies, X-rays, blood tests, etc. Additionally, the data can be fitness related, such as exercise routines, exercise goals, diets, virtual expeditions based on exercise routines, competitions, and the like, for example. The API facilitates access to all of this data for storage, retrieval, and other access. Applications can access this data to add value to the data, for example, an application can allow an insurance company to enter insurance information for a user, and a doctor's office can access this information upon doctor's visit by the user to mitigate the need for the user to show an insurance card. Taking this example further, a doctor can input information about a prescription under the user's account and a pharmacy can retrieve this information, as well as the insurance information, to fill the prescription for the user mitigating the need for the user to show proof of insurance and a prescription slip upon pick-up. Thus, the API can provide many applications with valuable access to personal health and fitness related data to add value and streamline current processes in the health and fitness fields.

To the accomplishment of the foregoing and related ends, certain illustrative aspects are described herein in connection with the following description and the annexed drawings. These aspects are indicative of various ways which can be practiced, all of which are intended to be covered herein. Other advantages and novel features may become apparent from the following detailed description when considered in conjunction with the drawings.

DETAILED DESCRIPTION

An application program interface (API) is provided to facilitate accessing a health integration network. The API can receive and process requests from applications to retrieve, store, modify, or otherwise access data within the health integration network and can provide authentication/authorization functionality. The API can receive requests in an extensible data form, such as extensible markup language (XML) according to an XML schema; additionally, the API can respond to such requests with XML representing a data set of information related to the request according to an XML schema. The API operates with numerous devices and applications such to effectively create a central storage for personal health and fitness related data with an easy to use, complete, and lightweight API. Applications can use system data types as well as specify their own types which can be shared with other applications to facilitate cross-application operability where no such open-ended system exists. The extensible data form used to communicate between the applications and the API achieves this by allowing virtually any kind of information to be stored along with data that describes how the data is stored, how it can be transformed, stylized, and/or schematized. It is to be appreciated that the data can also be stored and obtained in a non-structured or non-schematized manner.

Various aspects of the subject disclosure are now described with reference to the annexed drawings, wherein like numerals refer to like or corresponding elements throughout. It should be understood, however, that the drawings and detailed description relating thereto are not intended to limit the claimed subject matter to the particular form disclosed. Rather, the intention is to cover all modifications, equivalents and alternatives falling within the spirit and scope of the claimed subject matter.

Figure 1:
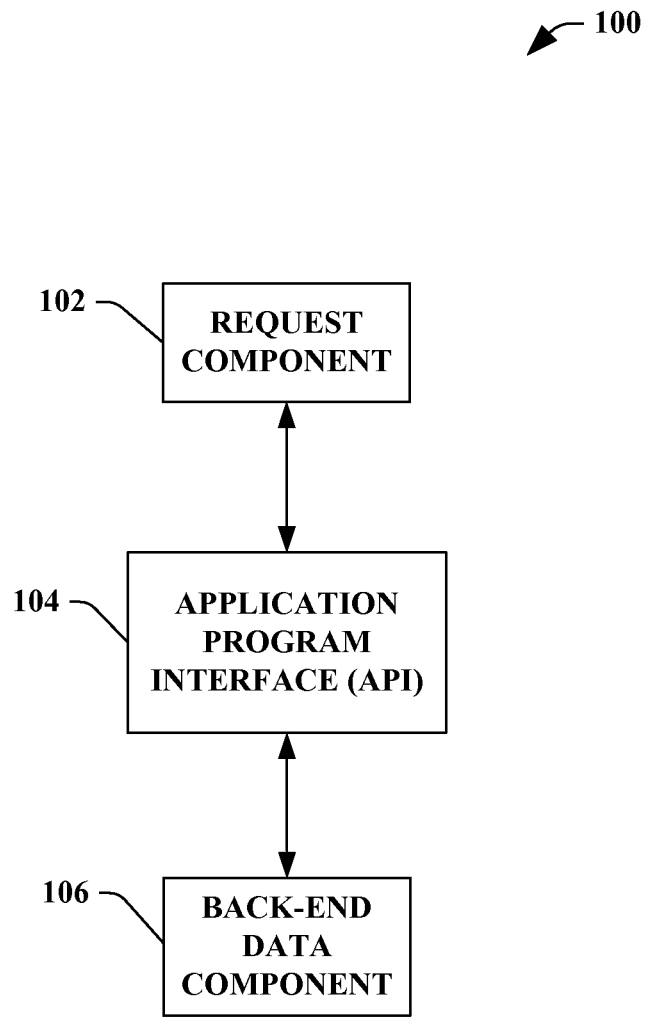
FIG. 1 illustrates a block diagram of an exemplary system that facilitates utilizing an API to communicate data between request and back-end data components.

Now turning to the figures, FIG. 1 illustrates a system 100 that facilitates data storage and retrieval, which can be utilized to participate in a health integration network. A request component 102 can specify a request for data retrieval, data storage, and the like to an API 104, which can interpret the request and query a back-end data component 106 based on the request. The back-end data component 106 can then respond to the API 104, which can at least return a result to the request component 102. The request component 102 can be any device capable of communicating with the API 104 such as by making requests. Possible requests include, but are not limited to, those made for authentication/authorization of the request component 102, storage of data, retrieval of data, modification of data, and any value-add service to the data, such as addition of data units, retrieval and application of styles and schemas regarding the format of the data, user interface and layout of the data and the like.

The API 104 can be utilized to interpret requests from the request component 102 to facilitate communication with the back-end data component 106. The requests sent by the request component 102 can be calls made via XML over hypertext transfer protocol (HTTP), calls made directly to the API 104, and/or calls made to a wrapper around the API 104. Using XML allows for an extensible data model where the structure can change and not require new code to interpret the data. This is due to the self-describing ability of XML, especially when used in conjunction with an XML schema. In addition, the API 104 can provide a layer of security over the back-end data component 106 to allow only authorized request components to access certain data in the back-end data component 106. In accordance with the present subject matter, the back-end data component 106 can house information related to personal health, which comprises a vast store of information. Such information can be relatively static (e.g., height, weight, medical history (personal and family), diseases, allergies, insurance, etc.), event-specific (e.g. workout regimen, workout vitals and statistics, current drug prescriptions, medical diagnoses, etc.), fully-dynamic (e.g., blood pressure, heart rate, diet, etc.), and the like. The API 104 can allow and limit access to all of this information to certain individuals based on the subject person's desires or doctor's orders, etc.

Furthermore, the API component 104 can be utilized to trigger events, provide real-time updates (for example, via callback function, etc.), receive alerts, and the like. Furthermore, the request component 102 can be such that receives events or alerts. Such events or alerts can occur upon entering data that crosses a threshold (e.g. high blood pressure), absence of needed data (e.g. missed blood-sugar level reading), occurrence of a real-world event, obtaining a milestone or goal, expiration of data, and the like. Thus, the subject matter presented herein provides for centralized storage and access of personal health related data to allow advantageous tracking of such data and streamlined communication of the data between parties to whom the data has value. Additionally, values returned or sent from the API 104 back to the request component 102 can be a return call from the original call (when utilizing a software development kit for example), XML over HTTP, etc.

Figure 2:
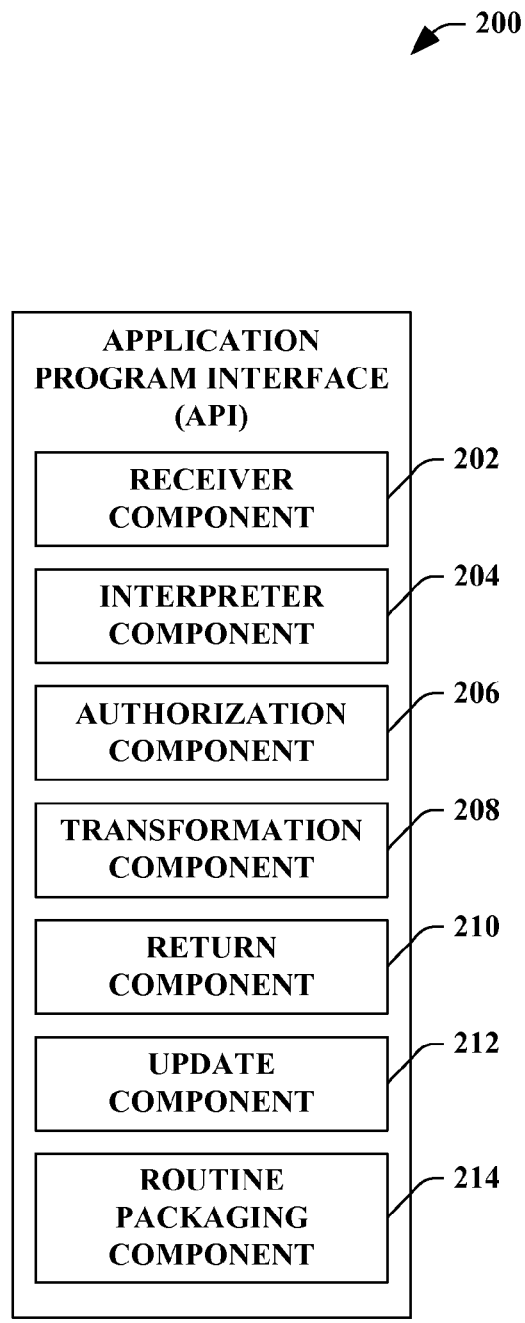
FIG. 2 illustrates a block diagram of an exemplary API.

Referring to FIG. 2, an API 200 is shown having various components to facilitate requests to retrieve, store, modify, or otherwise access data in accordance with the described subject matter. The API 200 can have a receiver component 202 that receives requests for data access, a interpreter component 204 that interprets the request and gathers the desired data and any related data and/or metadata (data about the data). The API 200 can also comprise an authorization component 206 to apply authorization/authentication rules to the requesting entity to ensure it has sufficient access to make the desired request. The API 200 can have a transformation component 208 that can apply a transformation, translation, style, and/or a schema to the data if desired. The transformation 208 can also package the resulting data with the appropriate and/or available transformation information so the requesting entity can perform desired transformations. The API 200 can also leverage a return component 210 to send the desired data, as well as any attached data, back to the requesting entity. An update component 212 can also be provided to allow applications to attach to the API 200, opening a communications channel, and automatically receive updates for information. The API 200 can further provide a routine packaging component 214 for creating intelligent routines to ease use of the API 200.

In utilizing the API 200, a requesting entity, such as a device, application, device running an application, legacy device attached to a system with an application, and the like, can initiate a request for data to the API 200, which is picked up by the receiver component 202. The request can be to access personal health and/or fitness related data, for example, such as prescription information. The receiver component 202 receives the request and sends it to the interpreter component 204. The interpreter component 204 determines the type of request, for example for retrieval of data, storage of data, or modification of data, and determines the record or type being requested. The interpreter component 204 can leverage the authorization component 206 to determine if the requesting entity has sufficient privileges to access the requested data for the type of request presented. For example, a party may not have sufficient access to change or even view a medical diagnosis of their spouse. Authorization rules can be set by many parties, including the person to whom the data directly relates, medical professionals, etc. If the entity is denied access, the return component 210 can send a resulting error notification (in XML format, for example) back to the requesting entity.

If access is granted, the interpreter component 204 can access relevant data, in the prescription example, this can include prescription name, a type code, instructions, volume, an image of the prescription with doctor's signature, etc. This information can then be passed to the transformation component 208 which can determine the information sought by the requesting entity and any transformations requested. For example, perhaps the requesting entity did not request the picture of the prescription; the transformation component 208 can apply a schema to grab everything but the picture from the instructions sent by the interpreter component 204 such that the need to send the picture, which may require significantly more bandwidth than sending only the textual information, is mitigated. Additionally, perhaps the requesting entity wanted a translation of the type code for the prescription, for example, the code might represent anti-inflammatory medication and the requesting entity would like display this information to the user. Also, perhaps an explanation of active ingredients and/or side-effects can be returned based on the type code—the transformation 208 can gather this information as well if requested. After all information desired is gathered, the return component 210 can send the data back to the requesting entity in the format requested, for example extensible mark-up language or any return type. An accompanying schema can also be returned describing the layout of the returned data.

The update component 212 can provide another type of data access where a communications channel, a pipe for example, is opened between an application (or other receiving component) and the API 202. As data flows through an underlying system, such as a health integration network, the update component 212 can automatically notify (or alert) a connected application of certain data, provided the application has authorization to attach to the data. This update component 212 facilitates an event based system where alerts can be sent to different users based on real-time occurrence of an event or data crossing certain thresholds. For example, if a blood pressure received a number (exceeding a threshold) of consistent high blood pressure readings, an event can be sent to a doctor's office system to notify and request an appointment. The information can also be sent back to the blood pressure monitor to notify the user of the number of high readings and that an appointment request has been sent to their doctor. There can be a number of similar scenarios available by utilizing an update component 212. Similarly, the open channel can automatically provide data to the health integration network if, for example, the device is one that sends constant updates. For example, a treadmill operated by a user can take constant heart rates during a session and open a channel to update the health integration network with this information, and other information concerning the workout routine for example, in real-time. It is to be appreciated that the open channel is not required; rather the API 200 can automatically, for example, call an API 200 on the application (such as a callback type function) to notify of an alert or update.

The routine packaging component 214 can provide a number of different functionalities to aid an application developer in utilizing the API 200 to create a third party application. For example, the routine packaging component 214 can tie together a set of commonly utilized routines into a single call or present them in a packaged presentation to give the developer what they really need to get started with the API 200. Additionally, routines can be provided to create XML and associated schemas that are commonly used with the underlying system, such as a health integration network, to create things such as data types and different records to be stored in the network. Moreover, artificial intelligence can be employed to determine the packaging of routines or creation of additional easier-to-use routines. These created routines can be a single call provided to the developer to perform a somewhat enhanced task such as a single call to get related data that is not necessarily stored together, for example a GetLastExerciseRoutine can be created to retrieve a user's last exercise session information as well as any heart rate taken around this time. As mentioned, a determination can be made (using artificial intelligence for example) that these functions are often called together, and then to create a single routine that accesses the data to make it easier for the application developer who may want this data together. It is to be appreciated that the aforementioned scenarios are just examples and the subject matter is not so limited.

Figure 3:
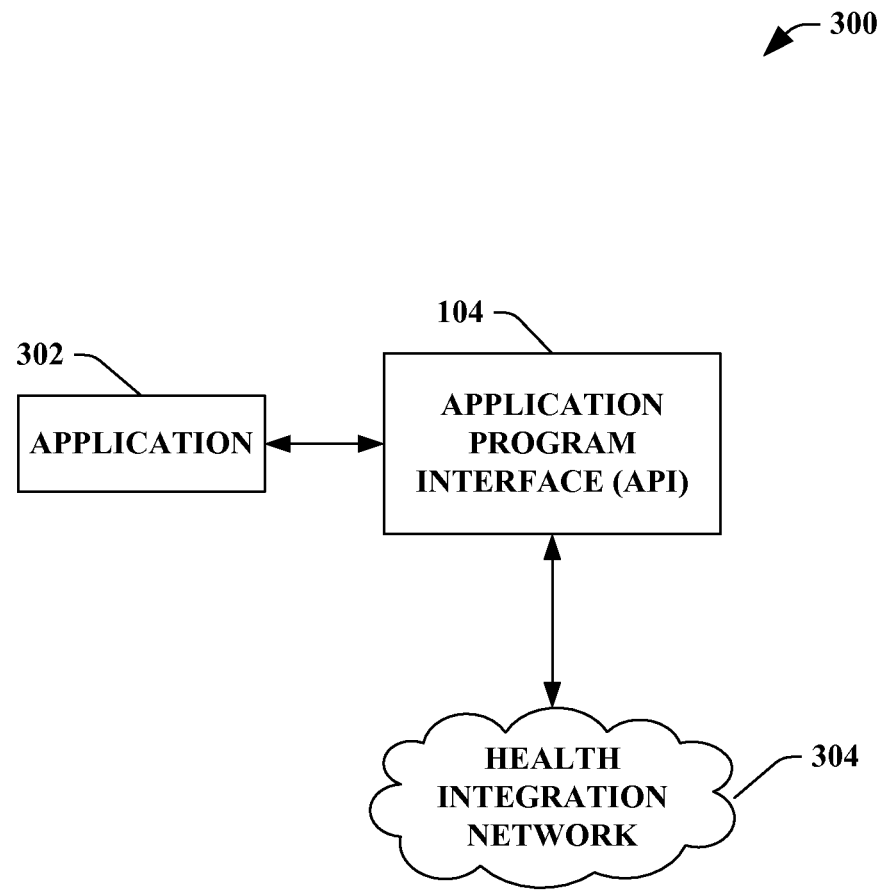
FIG. 3 illustrates a block diagram of an exemplary system that facilitates utilizing an API to communicate data between an application and a health integration network.

FIG. 3 illustrates a system 300 that facilitates utilizing an API 104 to interpret requests for data storage, retrieval, and the like from an application 302. The API 104 queries a health integration network 304 based on the request from the application 302 to return data to the application 302 based on the response from the health integration network 304. The application 302 can be a software application, executing on a computer or other device, a device itself, a device coupled to a computer or application, for example in a legacy device context, or the like. Example devices include any medical or personal health device such as those having outputs (e.g. blood pressure monitor, weight scale, blood/sugar level monitor, IV, pacemaker, stethoscope, x-ray, etc.), personal fitness tracking devices (combination heart rate monitor watches, pedometers, bicycle equipment (such as speedometers, altimeters, odometers, etc.), stop watches, and the like), and other applications including user interfaces for personal use and medical use. Thus, a doctor can store patient-specific information manually from a prescription, diagnosis or other chart, and individuals can store information about diet, workout regimen, medical insurance, etc. Data can be of any type and can have associated type definitions, schemas describing the layout of the data, and style parameters describing how the data can be presented. It is to be appreciated that the application 302 can be connected such to make direct requests to the API 104, but also in an open channel (or pipe) connection taking advantage of the update functionality.

As one example, a patient can utilize an application 302 to enter insurance and pharmacy information. The application 302 can submit this to the API 104 which can request storage in the health integration network 304. Then if the patient goes to the doctor's office, the receptionist can retrieve the insurance information through the same, or a separate, application 302 which requests the information using API 104. API 104 retrieves the insurance information for the patient from the health integration network 304 and transmits it to the API 104, which transmits to the application 302. This mitigates the receptionist having to ask for the patient's insurance card. Subsequently, during an appointment, the doctor can use the same, or different, application 302 to enter a medical prescription for the patient; the prescription is stored in the health integration network 304 via API 104. At this point, an alert can be sent to the patient's pharmacy that is also running the same, or a different, application 302 requesting fulfillment of the prescription. Alternatively, the patient can go to the pharmacy and request the prescription be filled and the pharmacy need not obtain a prescription from the patient as the information is stored in the health integration network 304. The pharmacy can use its application 302 to access API 104 to retrieve prescription and insurance data from the health integration network 304 for that patient.

As another example, the application 302 can be a device such as a blood pressure monitor, which can make a request to API 104 to store blood pressure for an individual, perhaps the blood pressure has been considered high for the last five readings, the blood pressure machine can receive an alert from the API 104 and notify the individual of this fact. Furthermore, an application 302 at a doctor's office for the individual can also receive this information via an alert from the API 104 to notify the doctor of the consecutive high blood pressure readings, and the doctor, or perhaps a personal trainer, can also tweak the patient's workout plan to include a few extra cardiovascular sessions and reduce salt in the diet, for example. The API 104 is not limited to the above examples, and in fact can perform a variety of methods with respect to data and the health integration network 304, including data auditing methods as well. Additionally, the application 302 can specify messages sent from the API 104 be encrypted by a public and/or private key where the application 302 has the private key to decrypt the data. In this way, more security is provided for the data communicated within the system to ensure privacy and authenticity. Moreover, the application 302 can set time-to-live values on the messages to allow them to expire when responses are not received in a given period of time. In this regard, the application 302 does not have to wait for messages to come back; rather the message can expire if, for example, the application 302 can find the information elsewhere more quickly.

Figure 4:
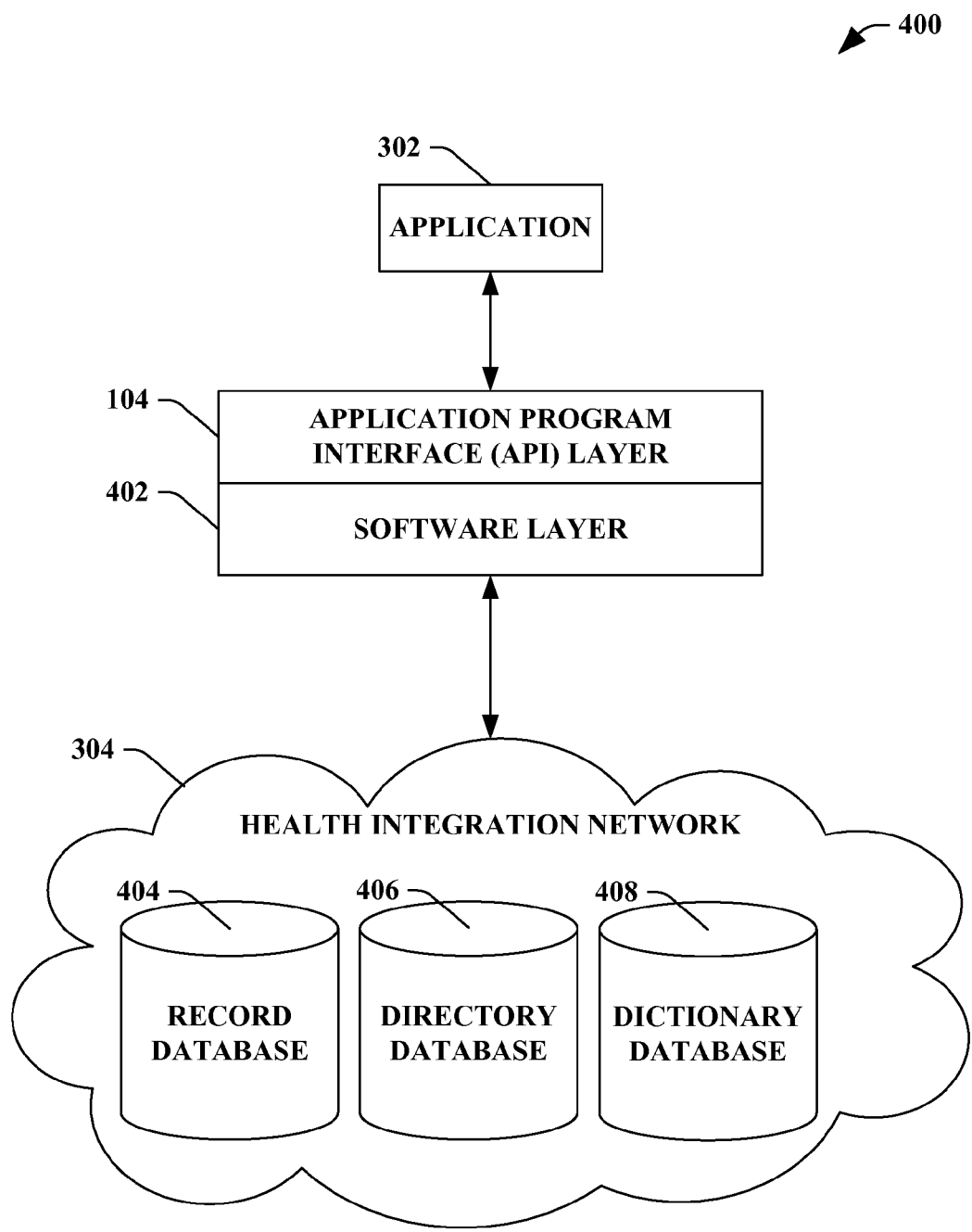
FIG. 4 illustrates a block diagram of an exemplary system that facilitates communicating personal health information.

Referring to FIG. 4, an example system 400 that facilitates accessing information within a health integration network is shown. An application 302 can at least one of display or specify health related data. It is to be appreciated that the application 302 can be many different types of applications including software applications, electronic devices executing a software application, electronic devices alone, legacy devices interfaceable with a device executing a software application, and the like. The application can utilize the API 104 to request and store data within a health integration network 304. It is to be appreciated that the API 104 can synchronously or asynchronously communicate with a plurality of applications 302 of similar or different types. The API 104 can also have a software layer 402 to leverage in interpreting and processing the request. The software layer 402 can be separated out as shown, or it can be integrated within the API 104, the health integration network 304, or both. Upon interpreting and processing a request from the application 302, the software layer 402 can access the health integration network 304 for any necessary data or to store necessary data to fulfill the request. The software layer 402 can also provide value-add to the data such as assembling data from the health integration network 304, applying business models or processes in conjunction with data, caching data, and/or applying transformations or additional information to/with the data. It is to be appreciated that there may be a plurality of APIs 104 and software layers 402 connecting to a centralized health integration network 304, and the centralized health integration network 304 may be a single system or distributed across multiple systems, platforms, and the like.

The health integration network 304 can comprise a plurality of data stores including a record database 404, a directory database 406, and a dictionary database 408. In addition, the health integration network 304 can comprise many other systems and/or layers to facilitate data management and transfer. Furthermore, the databases can be redundant such that multiple versions of each database are available for other APIs and applications and/or a back-up source for other versions of the databases. Additionally, the databases can be logically partitioned among various physical data stores to allow efficient access for highly accessed systems. Moreover, the databases can be hierarchically based, such as XML and/or relationally based. The record database 404 can be highly distributed and comprise personal health related data records for a plurality of users. The records can be of different formats and can comprise any kind of data (single instance, structured or unstructured), such as plain data, data and associated type information, self-describing data (by way of associated schemas, such as XSL schemas for example), data with associated templates (by way of stylesheets for example), data with units (such as data with conversion instructions, binary data (such as pictures, x-rays, etc.), and the like. Moreover, the record database 404 can keep an audit trail of changes made to the records for tracking and restoration purposes. Additionally, any data type or related instances of the foregoing information can be stored in a disparate database such as the dictionary database 408 described infra. The record database 404 can be partitioned, distributed, and/or segmented based on a number of factors including performance, logical grouping of users (e.g. users of the same company, family, and the like).

The directory database 406 can store information such as user account data, which can include user name, authentication credentials, the existence of records for the user, etc. The directory database 406 can also house information about records themselves including the user to whom they belong, where the record is held (in a distributed record database 404 configuration) authorization rules for the records, etc. For example, a user can specify that a spouse have access to his/her fitness related data, but not medical health related data. In this way, a user can protect his/her data while allowing appropriate parties (such as spouse, doctor, insurance company, personal trainer, etc.) or applications/devices (blood pressure machine, pacemaker, fitness watch, etc.) to have access to relevant data. In addition, the directory database 406 can comprise data regarding configuring applications 302 to interact with the health integration network 304; applications 302 can be required to register with the health integration network 304, and thus, the application data in the directory database 406 includes the registration information.

The dictionary database 408 can hold information relating to vocabulary definitions used by the health integration network 304 and requesting entities such as the API 104 and software layer 402. Such definitions can include data type definitions and information on how to display the different data types or transform them. Additionally, the dictionary database 408 can hold information for display layouts and templates, etc. Furthermore, the dictionary database 408 can hold different look-up tables that define codes through the use of standards and the like. For example, the dictionary database 408 can support International Classification of Diseases, ninth revision (ICD-9) released by the National Center for Health Statistics. These codes identify different diseases and diagnoses; thus a doctor can put one of these codes on a user's chart in the health integration network 304, and the dictionary database 408 can allow the software layer 404 (or API 104) to translate this code into something that makes more sense to the user, such as medical name and/or different, other, or additional information concerning the diagnosis. The dictionary database 408 can also be used to retrieve other metadata such as plural and abbreviated forms of codes (such as ICD-9 codes). It can also hold information that allows conversion between different measurement units, such as between feet to meters, Fahrenheit to Celsius, pounds to kilograms, etc.

In one embodiment, the application 302, which can be more than one application, can make a call to the API 104 to request, store, or modify data, for example. The API 104 leverages the software layer 402 to process the call made by the application 302. The software layer 402 can then query its own internal cache or the health integration network 304 for desired data; additionally or alternatively, the software layer 402 can directly query one or a plurality of the databases 404, 406, and 408 for the desired data. The software layer 402 can serially or asynchronously query for data until all data is obtained from the health integration network 304. The software layer 402 can then manipulate portions of the data using other data it has obtained to formulate the result desired by the application 302 and return that result to the application 302 via the API 104. For example, an application 302 can request a user's blood pressure reading by calling the API 104, which in turn can communicate with the software layer 402 to formulate the desired reading. The software layer 402 can query, directly or through the health integration network 304, the directory database 406 to obtain the location of the blood pressure reading, the dictionary database 408 to obtain schema, style, and general type information for blood pressure types, and the record database 404 to obtain the actual reading. Using the schema, the software layer 402 can interpret the record as two integers representing a systolic and diastolic pressure (and perhaps a pulse rate), and return these numbers to the application 302 through the API 104, or also apply a style, units, or other template to the numbers and return the result whether it be a string, XML, HTML, a picture, or the like. Additionally, the software layer 402 can return the raw data along with the transformation, style, and/or schema information to the application 302 through the API 104 to allow the application 302 to apply the these at will. Also, the software layer 402 can store the result in cache memory for future access. It is to be appreciated that the subject matter described is not so limited to the foregoing example/embodiment, but rather this is one of many possible embodiments of the API 104 that interfaces with a health integration network 304.

Figure 5:
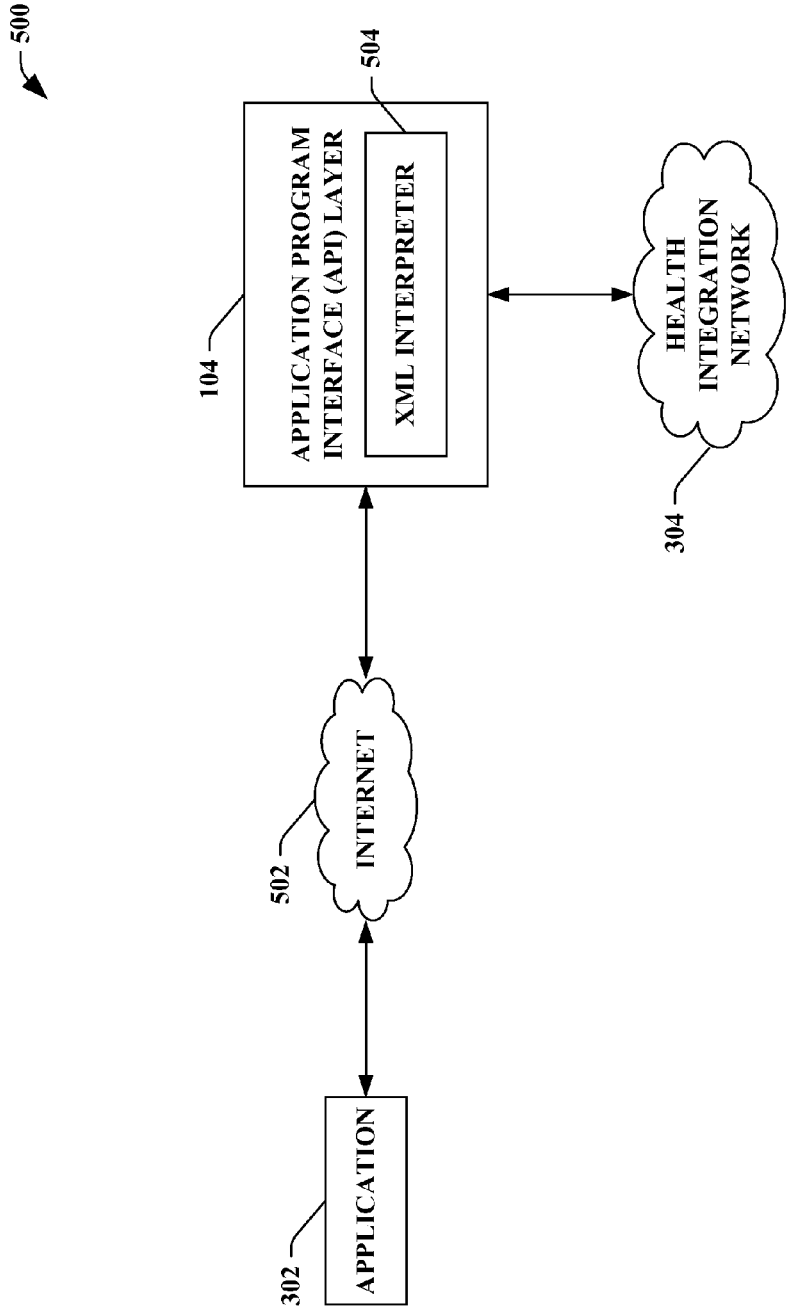
FIG. 5 illustrates a block diagram of an exemplary system that facilitates requesting personal health information from an API.

Turning now to FIG. 5, a system 500 in accordance with an embodiment of the subject matter disclosed herein is shown. The system 500 comprises an application 302 that makes a request to at least one of retrieve, store, modify, or otherwise access data from a health integration network 304. The request can be sent to the API 104 through the Internet 502 using an HTTP protocol specifying the request in XML format. The API comprises an XML Interpreter 504 to derive the request parameters from the request sent by the application 302. Requests for data can be submitted to the API 104 in XML form, as described, and the XML Interpreter 504 can require the XML to adhere to an XML schema to be considered a valid request. Requests can, for example, specify information such as a signature for authorization/authentication or security token type purposes of the application, a list of parameters (which can include the method name), the person ID (if the requesting party is different from the user whose information is sought, for example, a doctor accessing patient records), record ID (if a record is being manipulated for example), an authentication token for the user, a language specification, a country specification, a message creation time and expire time, and/or any parameters required by the method. A sample XML request sent to an API in accordance with an embodiment of the subject matter described can look like the following.

```
<request>
    <sig digestMethod="sha1"
        sigMethod="rsa-sha1"> ... </sig>
    <params>
        <method>GetThings</method>
        <target-person-id/>
        <record-id>1</record-id>
        <auth-token> ... </auth-token>
        <language>en</language>
        <country>us</country>
        <msg-time>2006-07-11T22:18:13Z</msg-time>
        <msg-ttl>330</msg-ttl>
        <info>
            <group>
                <filter>
                    <type-id>3d34d87e-7fc1-4153-800f-
                    f56592cb0d17</type-id>
                </filter>
                <format>
                    <section>core</section>
                    <section>xml</section>
                </format>
            </group>
        </info>
    </params>
</request>
```

In this example, the sig tag includes information regarding encryption of data with respect to a private key of the requesting application certificate, the params section shows the specifics of the request. In particular, the method tag specifies the method name and various entries and enumerated above. Specifically, the info section includes and parameters required by the method being called. In this case, GetThings requires a type-id that identifies the type of information being retrieved (weight, blood pressure, medication, etc.) as well as section parameters that specify which sections should be returned if there is more than one. It is to be appreciated that other info elements can be supplied to ensure the appropriate data is requested; thus the XML API calls are extensible to accommodate additional information and types that may reside in the health integration network. It is to be appreciated that the subject matter disclosed is not so limited to XML over HTTP requests, rather this is just one of many ways for an application to communicate with a health integration network through an API.

Responses to the record data requests can also be in XML form and transmitted back from the API 104 to the application 302 over HTTP via the Internet 502. These responses can include status codes (numeric and descriptive), any resulting data (called a "thing" in this example and described further infra) along with units, styles, schemas, and the like. For example, a response from an API call in accordance with the subject matter described herein may look like the following.

```
<response>
    <status>
        <code>0</code>
        <description>OK</description>
        <details />
        <exception />
    </status>
    <ad />
    <wc:info xmlns:wc="methods.response.GetThings">
        <group>
            <thing>
                <thing-id>1</thing-id>
                <type-id name="Weight">3d34d87e-7fc1-4153-800f-f56592cb0d17</type-id>
                <eff-date>2006-07-11T20:51:25Z</eff-date>
                <system-sets>16</system-sets>
                <data-xml>
                    <weight>
                        <value unit="lbs">204.8</value>
                    </weight>
                </data-xml>
            </thing>
        </group>
    </wc:info>
</response>
```

It is to be appreciated that the subject matter described herein is not so limited to the above request and response examples, but rather these are just examples of XML over HTTP request/response conventions. As noted, there are many ways for an application 302 to communicate with the API 104 such as an exposed Software Development Kit (SDK) object model compatible with many supported languages (such as .NET, Java, etc.), as shown infra, as well as an SDK object model and XML.

Figure 6:
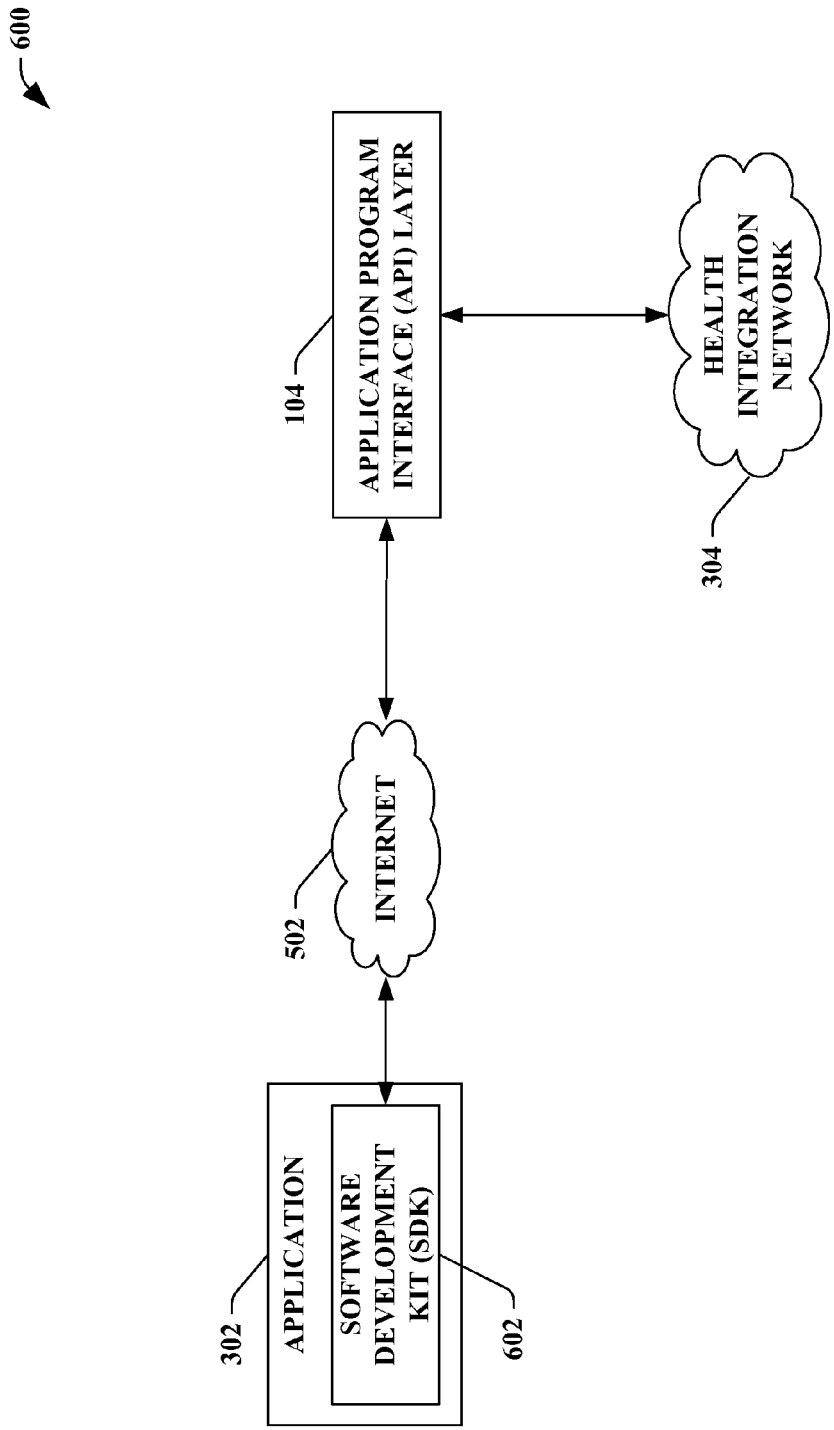
FIG. 6 illustrates a block diagram of an exemplary system that facilitates requesting personal health information from an API using a software development kit (SDK).

Turning now to FIG. 6, a system 600 for accessing data from a health integration network in accordance with an embodiment of the subject matter described herein is presented. An application 302, which is an application that can access a health integration network 304, is provided with a software development kit (SDK) 602. The SDK 602 enables the application to make calls to request, store, modify, or otherwise access data stored in a health integration network 304. An API 104 is provided to facilitate communication with the health integration network 304.

The application 302 can leverage the SDK 602 to make calls to the API 104. The SDK 602 is implemented to offer at least a portion of the functionality comprised by the API 104. For example, the application need only communicate with the SDK 602 to retrieve, store, and modify data in the health integration network 304. The application 302 can initialize the SDK 602 at which point it can utilize the SDK 602. Typically, once initialized, the application 302 can make function calls on the SDK 602 through a dot notation form such as expressed in the pseudo-code below.

```
public void DisplayWeightToConsole(string serviceUrl, string authUrl)
{
    WService service =
        new WService(
            appId,
            serviceUrl,
            authUrl,
            "test",
            "test");
    PersonInfo personInfo = service.GetPersonInfo( );
    // Note, this assumes that the person is authorized
    // for exactly one record.
    RecordInfo record = personInfo.AuthorizedRecords[0];
    ReadOnlyCollection<ThingInfo> weightMeasurements =
        record.GetThingsByType(
            new Guid("3d34d87e-7fc1-4153-800f-f56592cb0d17"),
            ThingDataSections.Core | ThingDataSections.Xml);
    // This outputs the XML data of each weight measurement
    foreach (ThingInfo weight in weightMeasurements)
    {
        Console.WriteLine(weight.XmlData.OuterXml);
    }
}
catch (Exception e)
{
    Console.Error.WriteLine(e.Message);
}
}
```

It is to be appreciated that the above psuedo-code is merely an example of using an embodiment of the present subject matter with an SDK and the subject matter is not so limited. When the application 302 makes calls to the SDK 602, such as record.GetThingsByType . . . , the SDK 602 is implemented to make a subsequent call to the API 104 to retrieve, store, or modify data via the Internet 502 (if the health integration network components are remotely stored). The SDK 602 makes this interaction appear seamless to the application 302. Upon making appropriate requests to the API 104, the API 104 and/or possible software layer request relevant data from the health integration network 304. The request may comprise one or more requests to one or more disparately or locally stored databases as described above. Once relevant information is gathered, the API 104 and/or possible software layer can apply transformations, styles, and/or schemas to the data before submitting it back to the SDK 602 through the Internet 502.

For both FIG. 5 and FIG. 6., it is to be appreciated that accessing the health integration network 304 and/or API 104 is not limited to Internet communication, rather where the components are located on the same local area network (LAN), LAN communication can be utilized as well as WAN, WLAN, or the like. Any mode of communicating data between two systems can be used. Moreover, any sort of data communication/specification over the Internet or otherwise can be used as well. Additionally, the API 104 will likely return from a call made from the application 302 with at least one status code (as indicated in the sample XML above); this code can be something like the following list of status codes.

| Code | Description | Reason |
|---|---|---|
| 0 | OK | Success |
| 1 | FAILED | General failure, cause unclear |
| 2 | BAD_HTTP | HTTP protocol problem |
| 3 | INVALID_XML | The request XML can't be parsed or is non-conformant. |

-continued

| Code | Description | Reason |
|---|---|---|
| 4 | BAD_SIG | Signature validation failed on the request. |
| 5 | BAD_METHOD | The requested method does not exist. |
| 6 | INVALID_APP | The application specified does not exist, is not active, or the calling IP address is invalid. |
| 7 | TOKEN_EXPIRED | The authentication token has expired. |
| 8 | INVALID_TOKEN | The authentication token is malformed or otherwise busted. |
| 9 | INVALID_PERSON | The person does not exist or is not active. |
| 10 | INVALID_RECORD | A record with the specified ID does not exist. |
| 11 | ACCESS_DENIED | The person or application does not have sufficient privileges to perform the operation. |
| 12 | NYI | Not yet implemented. |
| 13 | INVALID_THING | A thing with the specified ID does not exist. |
| 14 | CANT_CONVERT_UNITS | The units specified for the value of a thing cannot be converted to the unit type of existing things of this type. |
| 15 | INVALID_FILTER | Missing or invalid filter specified to GetThings. |
| 16 | INVALID_FORMAT | Missing or invalid format specified to GetThings. |
| 17 | APPACCEPT_MISSING | The application requires the user to accept the application agreement. |
| 18 | INVALID_APPAUTH | The application is not authorized for use by this person. |
| 19 | INVALID_THING_TYPE | The specified thing type does not exist. |
| 20 | THING_TYPE_IMMUTABLE | The thing cannot be updated because it is immutable. |
| 21 | THING_TYPE_UNCREATABLE | Things of this type can only be created by the system. |
| 22 | DUPLICATE_CREDENTIAL_FOUND | The specified logon name already exists. |
| 23 | INVALID_RECORD_NAME | An invalid record name was specified. |
| 24 | DRUG_NOT_FOUND | The specified drug could not be found. |
| 25 | INVALID_PERSON_STATE | An invalid person state was specified. Valid person states include: Active, Suspended, and Deleted. |
| 26 | INVALID_CODESET | The specified code set could not be found. |
| 27 | INVALID_GROUP | The specified group does not exist, is invalid, or is not active. |
| 28 | INVALID_VALIDATION_TOKEN | The email validation token specified is invalid. |
| 29 | INVALID_ACCOUNT_NAME | The person account name cannot be null or empty. |
| 30 | INVALID_CONTACT_EMAIL | The email name cannot be null or empty. |
| 31 | INVALID_LOGIN_NAME | The login name cannot be null or empty. |
| 32 | INVALID_PASSWORD | The password cannot be null or empty. |
| 33 | INVALID_OPENQUERY | An open query with the specified ID cannot be found. |
| 34 | INVALID_TRANSFORM | The transform cannot be loaded. |

-continued

| Code | Description | Reason |
|---|---|---|
| 35 | INVALID_RELATIONSHIP_TYPE | The relationship type is invalid. |
| 36 | INVALID_CREDENTIAL_TYPE | The credential type is invalid. |
| 37 | INVALID_REQUEST_PARAMETERS | The required parameters were missing or prohibited parameters were found. |
| 38 | APP_AUTH_NOT_REQUIRED | The application does not require application authorization. |
| 39 | VOCABULARY_NOT_FOUND | The requested vocabulary item(s) could not be found. |
| 40 | DUPLICATE_AUTHORIZED_RECORD_FOUND | This is a short term status code which will be removed when merger of authorizations is implemented for record authorization performed at an app's behest. Indicates that the person already has record authorization (though the permissions, relationship type, whether primary, etc may be different |

Figure 7:
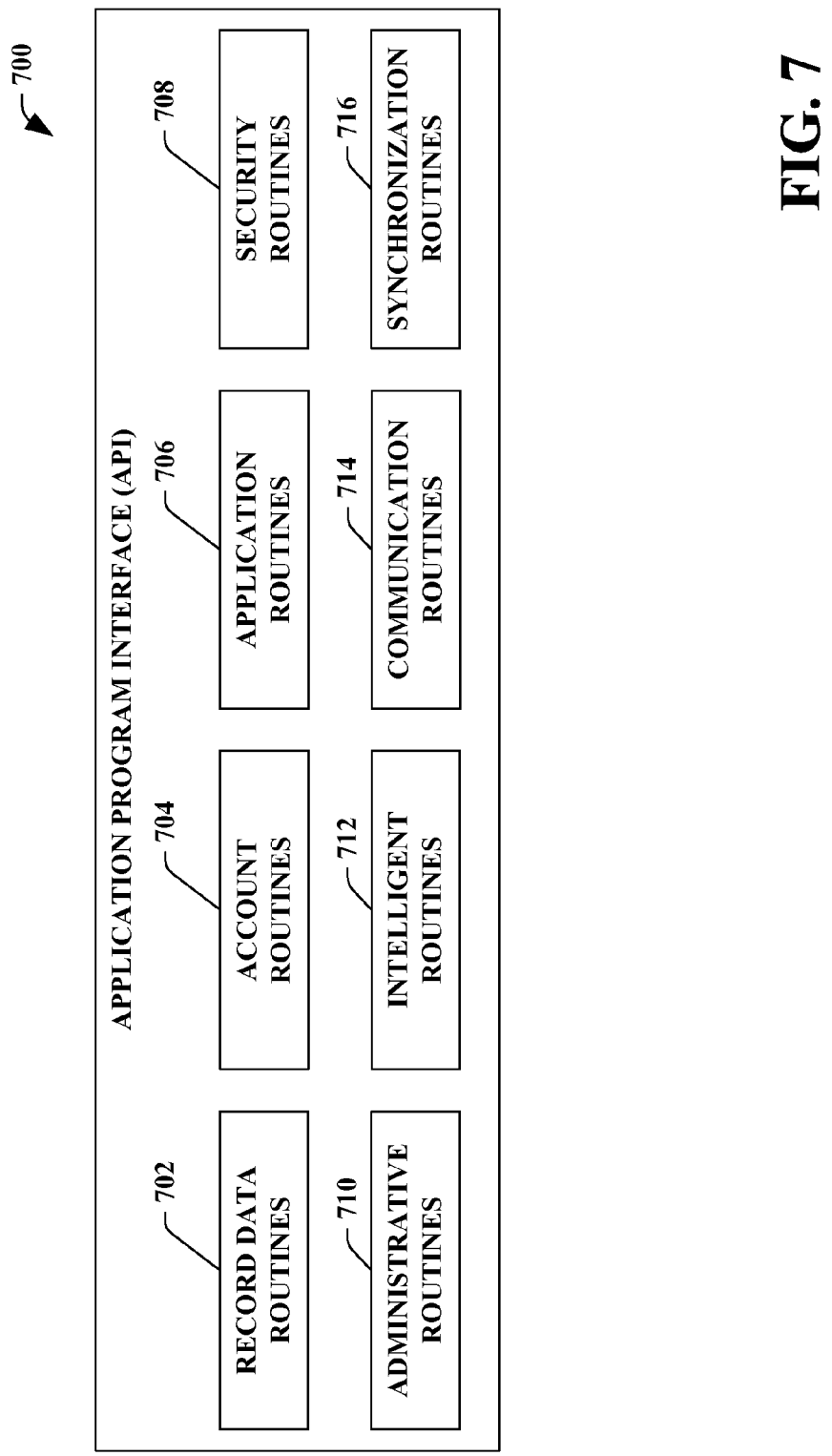
FIG. 7 illustrates a block diagram of an exemplary API.

Referring to FIG. 7, an API 700 is illustrated comprising various groups of routines, which provide different ways of accessing different data. Record data routines 702 comprise multiple routines that allow an application 302 (from FIG. 4) to request, store, modify, or otherwise access record data stored in the health integration network 304 (from FIG. 4). Such data can include data in the three databases 404, 406, and 408 (from FIG. 4), data itself as well as data that describes the data, related binary data (such as pictures, x-rays, and the like), etc. Data associated with a record and defined by a type will be referred to herein, in examples and routine names, as a "thing." The record data routines 702 can comprise routines such to query data from health records stored in the health integration network. Things can come in the form of structured data (XML), binary data (images), and the like; they represent a single instance data in the health integration system and are typically associated with a type and metadata (which can have a type for the value, units of measurement, comments, the origination point of the data, etc.). For example, a GetThings routine can be provided to retrieve this information as shown in examples above. This routine, which can be called, using XML over HTTP for example, can require an XML input specifying the routine to be called and further comprising an "info" section to specify filters for the data query; the filters can include any of the following.

| Filter | Definition |
|---|---|
| id | Any number of thing IDs can be specified. This clause is OR'd with all other clauses and is specified outside the filter element. |
| type-id | The identifier for a single thing. |
| eff-date-min | Things with effective dates newer than the date specified. The date is in UTC time. |
| eff-date-max | Things with effective dates older than the date specified. The date is in UTC time. |
| created-app-id | The ID of the application that created the thing. This is a Guid. |
| created-person-id | The ID of the person that created the thing. This is a Guid. |
| updated-app-id | The ID of the application that last updated the thing. This is a Guid. |
| updated-person-id | The ID of the person that last updated the thing. This is a Guid. |
| created-date-min | Things with creation dates newer than the date specified. The date is in UTC time. |
| created-date-max | Things with creation dates older than the date specified. The date is in UTC time. |
| updated-date-min | Things with last updated dates newer than the date specified. The date is in UTC time. |
| updated-date-max | Things with last updated dates older than the date specified. The date is in UTC time. |
| xpath | If the thing type is represented as structured data (XML), an XPATH query can be specified to run against the data. The query can only check for existence. If the query produces a true result for the thing it is returned. This clause does not match against binary thing types. |
| set-id | Gets all things in the user-defined set. |

Additionally, the "info" section can specify one or more format sections to further determine what data is returned for things that match the specified filter as well as any transformations, styles, or schemas to be applied. When the request is sent to the API and the software layer processes the request and gathers data, the response is sent back to the requesting entity. The response can be an XML response, as shown above, with a grouping of matching thing results, status code, etc. The response can be conformed to and sent along with an XML schema that can define the layout of the response, and specifically, a GetThings routine response can conform to a schema defined for a thing, which can have multiple sections. The API gathers the sections specified in the request; the sections include a core section which can define effective dates of the record and member system-sets (high-level groups to which things can belong), an audit section which can define creation and update information of a record for future querying, an XML section containing XML representing data for the thing (if the type defines a schema, the data must conform to the schema), a BLOB section for binary data (such as an image/x-ray), an annotation section that can define one or more annotations which can also contain notes for auditing, a sets section that defines one or more user-defined sets to which the data belongs, and a permission section that outlines different authorization permissions for the thing. Similarly, the record data routines 702 can provide a PutThings routine for creating a new thing and/or updating an existing thing. The request can be of XML form as shown above and the thing to put can be required to conform to the above thing schema. This routine can return a result code and IDs of the created/updated things. Additionally, a RemoveThings routine can be provided to delete things where the request can contain similar elements as the GetThings request; however the specified things are deleted and not returned. Moreover, a GetAuthorizedRecords routine may be provided for querying known record ID for which the requesting entity has permission (e.g. the requesting entity is not the user to whom the data belongs). This routine can return the record according to and/or with a schema.

The API 700 can also provide a set of account routines 704 to manage the users and groups in the health integration network. For example, a QueryPersons routine can be provided that allows a requesting application to gather a reduced set of account information for users matching the filter criteria specified. To this end, a request can be required to conform to a request schema. Available filters may include name of the sought person, ID, e-mail address, etc., and can check if these elements contain any of the specified characters, returning the affirmative results; the results can be required to conform to a schema (XML or otherwise). Furthermore, a GetPersonInfo routine can be provided to request the account information for the requesting user, including name, e-mail address, validation status of the e-mail address, application settings, authorized records, etc. Additionally, similar group routines can be provided to allow users to belong to logical groups. The groups can be managed similarly as the users of the system. Thus, routines such as a GetGroups routine can be provided, for example, to retrieve information about a group including member IDs. Both the request and response can be required to comply with an XML schema to interpret the data.

In addition, the API 700 can provide application routines 706 for allowing registration and location of applications using the API 700 and health integration network. For example, a GetApplication routine can be provided to gather information regarding one or more applications registered with the health integration network; specified parameters can include name of the application and/or an ID if known. The routine can return one or more applications located (names and IDs), as well as whether the application requires authorization and/or acceptance, and the like. Moreover, an AddApplication routine can also be provided to register an application with the health integration network. The request can be sent as XML with parameters corresponding to an ID for the application (created using a certificate), name of the application, a public encryption key used to verify all requests, record-level authorizations, routine level authorizations, application settings (in XML form or otherwise), whether authorization is required to use the application, and whether acceptance is required to use the application. Acceptance can include steps such as accepting an end-user license agreement (EULA). The routine can return the ID of the application and a status code, for example.

Furthermore, the API 700 can include security routines 708 that manage security for the given things and/or records, for example. These routines can include a GetPermissions routine to obtain the permissions associated with authorized users for a given record, which can require an ID for the user and an ID for the record for which permission information is being requested. The routine can return, then, a set of rules associated with the record ID with respect to a user or group, permissions that may exist for the record, the things in the record to which the permissions apply, and any excepted things to which the permissions may not apply. Similarly, a GetAuthorizations routine can be provided to get the IDs of users or groups having access to certain things. To this end, a thing ID is provided along with a permission specification as input, and the routine returns a list of users and/or groups who have the level of access for the thing requested. Additionally, AddPermissions and RemovePermissions routines can be provided to set new permissions and delete permissions for given records. Also, the security routines 708 can comprise a GetEffectivePermissions routine to gather permission information on a record for a user that is also part of groups having varying permissions. This routine can attempt to provide the user with the best permission information whether it be due to group membership or user-level granted permission. More routines can be provided as well and can be, for example, routines that can only be utilized within a health integration network, for example (by management and/or other types of systems participating in the network). Moreover, routines for providing subscription functionality for users can be provided to subscribe to services offered by the health integration network on behalf of other applications and companies, for example. These can also include routines for providing incentives for system use, for example, promotions from different application providers, coupons for service use, etc.

As mentioned, though the example embodiments described supra are referenced in an XML context, other ways of providing such routines can be used, for example an SDK can be exposed using .NET, for instance, and can interpret calls in a dot notation/parameter specifying format rather than XML over HTTP. The parameters can be XML or other types of parameters, but the substantive data sent and received is the same as if XML over HTTP is used as in the previous examples.

The API 700 can further comprise a set of administrative routines 710 accessible only by those authorized to maintain the health integration network, such as customer service representatives. These routines can allow super-user level authorization to modify just about any thing and/or record in the health integration network. These routines can be implemented similarly to those above or within separate architectures to protect from potential hacking and the like.

The API 700 can also expose a set of intelligent routines 712. The intelligent routines 712 can be created and tuned to specific applications or packages to aid API use in third party application development. An example routine can help a developer to create an XML schema for data that the application plans on utilizing. This can enable a developer to quickly add new possible data values, types, and containers. This can also be performed in a batch mode and the routine can associate this information with the application. These routines can also be created by third parties as add-ons to the API 700 to facilitate simple access to rich data. For example, a company can expose a public routine to access its proprietary data using its trade name in the routine call name to additionally create a monetary incentive to promote development exposing the valuable data. It is to be appreciated that the API 700 and some routines can be located remotely while others located proximal, on, or within an accessing application. In fact, some routines can be downloadable to a device to allow for more expanded functionality and easier-to-use, more efficient routines. These can come in packages or individually downloadable, or even as automatic updates and can also be part of a software development kit.

Another example of intelligent routines 712 can be an alerting system functionality where following certain events in the system and/or some threshold being exceeded, the API can notify appropriate parties privy to the information. For example, if a blood-sugar level monitor received a number of low readings or one fatally low reading, the reading, upon being sent to the API 700, can trigger an intelligent routine 712 to notify EMS and/or emergency contacts enumerated in the health integration network. One can imagine devices created based solely on this functionality; perhaps an automated pulse detector that many people can wear all of the time will detect low or no pulse (or racing pulse) and notify authorities and/or emergency contacts. In addition, the device can be global positioning system (GPS) based or associated therewith and the API 700 can have the ability to obtain the GPS coordinates of the device and submit the coordinates to the alerted system/party. Thus, another intelligent routines 712 can decipher the GPS coordinates into an address and also to provide directions from a notified system's or user's current position. It is to be appreciated that the API 700 can offer such services in addition to the data functionalities, but is not so limited.

Moreover, communications routines 714 can be provided to facilitate automatically communicating information to users, devices, applications, and other entities within a health integration network, for example. Such communication can occur inside and/or outside the network. Inside communications can include events, alerts, updates, and the like; for example, a radiologist can direct an x-ray to a user's primary care physician's application. Other examples include health alerts, such as medical history announcements, change in prescription or information related thereto, appointment reminders, and the like. The outside communications can include, for example, electronic mail (e-mail), facsimile, instant message, and the like; in the previous example, the x-ray can be delivered as an e-mail to the primary care physician (via attachment, for example). Additionally, synchronization routines 716 can be provided to facilitate communicating between distributed health integration networks in accordance with the described subject matter. Specifically, more than one health integration network can exist and users can desire information stored in disparate health integration networks; thus the synchronization routines 716 can facilitate communication between the systems to achieve this end. It is to be appreciated that having multiple remotely located health integration networks provides efficient access in many parts of the world, and the synchronization routines 716 can provide a layer of security and/or privacy. In addition, the synchronization routines 716 can provide redundancy within the multiple health integration networks to facilitate greater data accessibility.

The aforementioned systems, architectures and the like have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component to provide aggregate functionality. Communication between systems, components and/or sub-components can be accomplished in accordance with either a push and/or pull model. The components may also interact with one or more other components not specifically described herein for the sake of brevity, but known by those of skill in the art.

Furthermore, as will be appreciated, various portions of the disclosed systems and methods may include or consist of artificial intelligence, machine learning, or knowledge or rule based components, sub-components, processes, means, methodologies, or mechanisms (e.g., support vector machines, neural networks, expert systems, Bayesian belief networks, fuzzy logic, data fusion engines, classifiers . . . ). Such components, inter alia, can automate certain mechanisms or processes performed thereby to make portions of the systems and methods more adaptive as well as efficient and intelligent, for instance by inferring actions based on contextual information. By way of example and not limitation, such mechanism can be employed with respect to generation of materialized views and the like.

Figure 8:
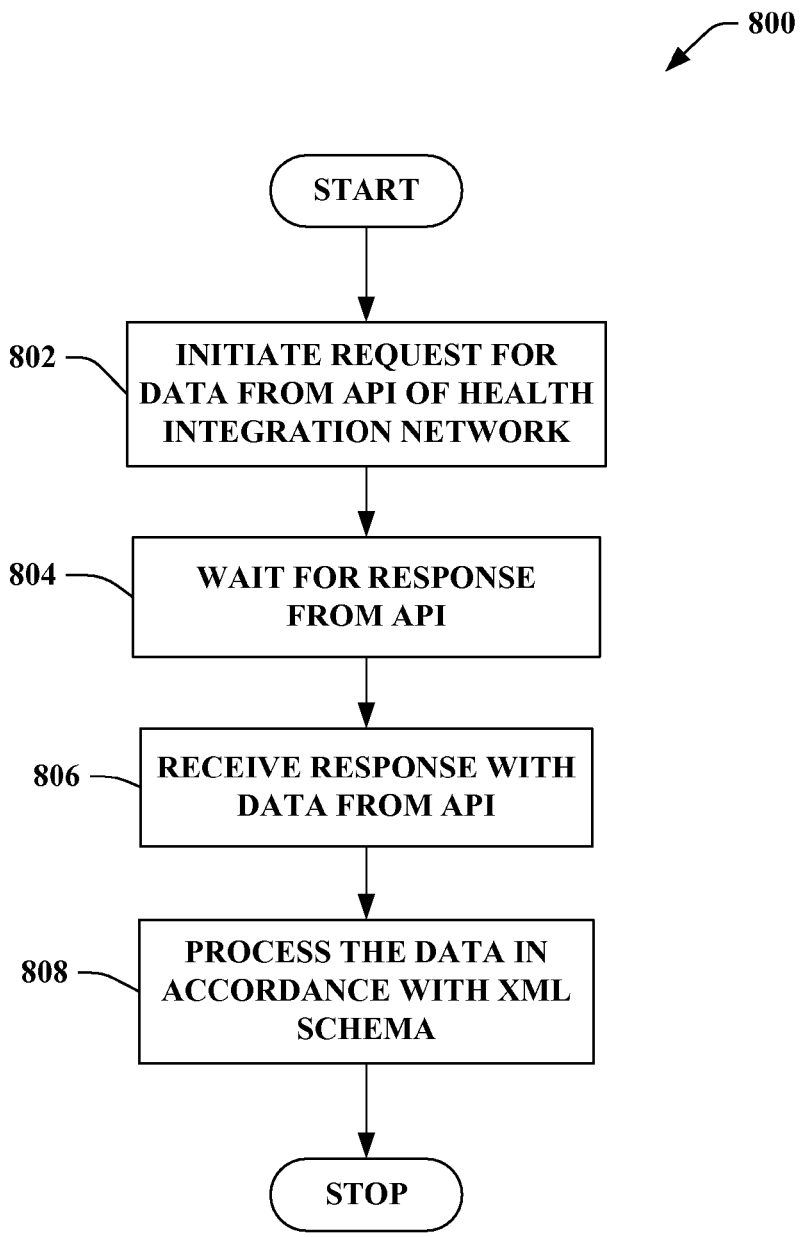
FIG. 8 illustrates an exemplary flow chart for requesting data from a health integration network using an API.
Figure 9:
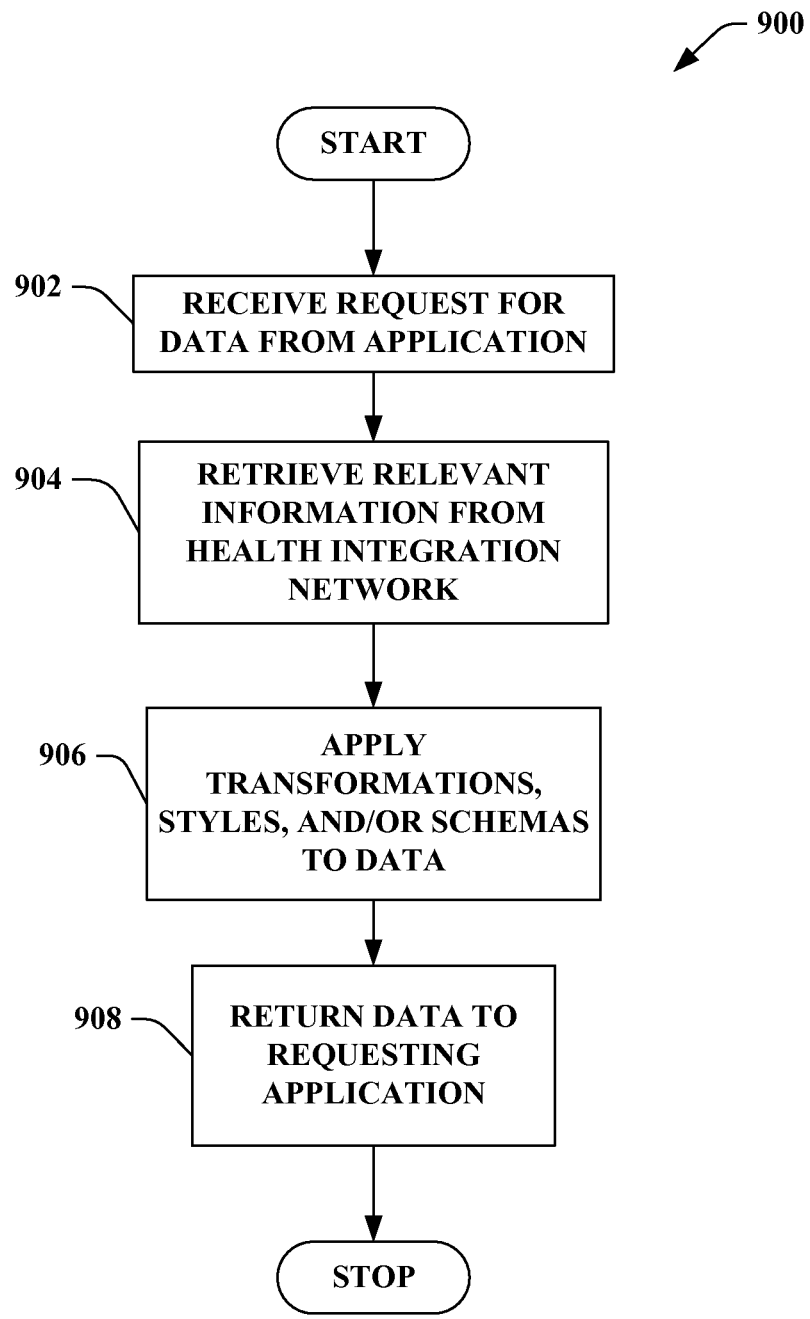
FIG. 9 illustrates an exemplary flow chart for processing a request for personal health information from an application.

In view of the exemplary systems described supra, methodologies that may be implemented in accordance with the disclosed subject matter will be better appreciated with reference to the flow charts of FIGS. 8-9. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 8 shows a methodology for an application requesting data from a health integration network via an API. The request can be for any data residing in a health integration network including any data about the requested data or other data. The request can be specified in a plurality of architectures including XML over HTTP, SDK, and/or both or a mixture of these architectures, as well as any request/response type architectures. The request can be of request/response type and/or subscription based where a data channel remains open upon request and updates are automatically directed to the channel and picked up by the requesting application. The latter form can be useful for alerts/alarms, automatic updates, and such as described supra. For example, an extremely low insulin level reading can cause an insulin monitor to send this information to the health integration network (this is request/response); the health integration network can then send an alert on an open channel for an application at a doctor's office and/or an application of an emergency contact (such as an application that can send pages and/or text messages) of the user' low insulin level mitigating the need to request this information (this is an example of a subscription based system). This particular methodology 800, however, displays request/response though it is to be appreciated a subscription-based method can be utilized in accordance with the subject matter described as well.

At reference numeral 802, the application initiates a request for data from an API of a health integration network as described herein. It is to be appreciated that the application can be required, first, to register with the health integration network via the API as described supra, which can be another form of request. Furthermore, requests can be to store data as well as query data in the health integration network. Also, the requesting application can be a number of devices, applications, or the like, with the ability to communicate with the API. For example, the application can be a 3rd party application traditionally operable with an external personal fitness device (such as a heart rate monitor watch) adapted to interface with the health integration network API to store and retrieve data gathered by the external personal fitness device. Additionally, the personal fitness device can be equipped with the technology to communicate to the health integration network through the API itself. Moreover, if the request is for data, the application can specify filters for query type functionality and also sections of data to retrieve. For example, if requesting X-ray information, the application may only want (and indeed may only be authorized to receive) administrative information; thus the request can specify this mitigating the need to transfer any X-ray images (which are presumably large compared to the other associated data) upon response from the health integration network.

After making the request, the application waits to receive a response from the API at 804. The request can be synchronous with respect to the application, meaning the application actually holds off other tasks while waiting for the request to return. However, the application can also make the request in an asynchronous context so the application can continue processing while waiting for a response. Typically, this functionality can be implemented with a call-back function, multiple spawned threads, etc. Additionally, the application can make other calls to the API while waiting for the current call to return.

At reference numeral 806, the API response is received by the application. The data can arrive in XML form, for example, with a specified status code. The XML can also comprise the resulting data from the request for data. The data can be in plain form along with transformation, style, and/or schema information, or as a string with these already applied. The application knows how to render and/or otherwise process the received information so the user of the application can optimally view the information and can do so according to an XML schema at reference numeral 808.

FIG. 9 illustrates a methodology 900 that facilitates requesting data from a health integration network via an API. The data can be any data described above as residing in the health integration network which may be distributed across a network and/or databases. The request can be for data alone, data and type information, data and transformation, style, and/or schema information, etc. Furthermore, as described supra, the request can be made by utilizing XML over HTTP, SDK, and/or a mixture of these, as well as any request/response platform.

At reference numeral 902, a request is received from an application for data. The request can be received by an API, a software layer, and/or a combination. As described, the request can be for any record available in a health integration network (and for records unavailable, though an error will likely ensue). It is to be appreciated that the API and/or software layer can perform additional processing with the request such as caching, auditing, etc. Additionally, the receiving entity may perform some authentication/authorization routines before continuing to request data from the health integration network. Alternatively or additionally, authentication and/or authorization can be performed by the health integration network.

At reference numeral 904, relevant information is retrieved from the health integration network. This information can be the data requested and/or additional data to help authorize, formulate, transform, stylize, or perform other actions on the requested data. The data can be obtained from one or a multitude of locally or remotely stored databases. Additionally, the databases can operate in conjunction with one another to provide seamless access to the data. A master database can be provided, for example, that has an indicator as to where the sought information resides and is able to retrieve the information. Thus, in one embodiment, the information only needs to be requested from the master database, or an interface therefor, and the master database knows where to locate the information and can return it to the requestor. Alternatively, the API and/or software layer knows or can acquire this storage information.

If the requested data comes with appropriate information, transformations styles, and/or schemas are applied to the data at reference numeral 906. For example, transformation may include from metric to US units such as kilograms to pounds, etc. A transformation may also include transforming a string or two integers into a blood pressure data structure of systolic and diastolic pressures, for example. Similarly, styles can include adding reference signs or characters such as rendering a height stored as 73 (an integer representing inches) to be in the form 6'1" for example. Additionally, schemas may be supplied with the data to describe the data layout for more complex data structures. The API and/or software layer can use this schema to extract certain relevant data or apply it to create a representation of the data. For example, as in the previous methodology, if the application only wants a portion of the data, such as administrative information about an X-ray and not the image itself, the schema can be applied to only send back the requested administrative data.

Then at 908, the data is returned to the requesting application. The data returned can be data alone, data with the aforementioned transformations, styles, and/or schemas applied, or both. The application, thus, can form the data to meet the needs of the requesting entity by utilizing all, a combination, or a portion of each of the transformations, styles, and/or schemas. It is to be appreciated that the extraneous transformation, style, and/or schema information for data can be separately requested as well and/or stored in a local cache of the application for later use.

As used herein, the terms "component," "system" and the like are intended to refer to a computer-related entity, either hardware, a combination of hardware and software, software, or software in execution. For example, a component may be, but is not limited to being, a process running on a processor, a processor, an object, an instance, an executable, a thread of execution, a program, and/or a computer. By way of illustration, both an application running on a computer and the computer can be a component. One or more components may reside within a process and/or thread of execution and a component may be localized on one computer and/or distributed between two or more computers.

The word "exemplary" is used herein to mean serving as an example, instance or illustration. Any aspect or design described herein as "exemplary" is not necessarily to be construed as preferred or advantageous over other aspects or designs. Furthermore, examples are provided solely for purposes of clarity and understanding and are not meant to limit the subject innovation or relevant portion thereof in any manner. It is to be appreciated that a myriad of additional or alternate examples could have been presented, but have been omitted for purposes of brevity.

Furthermore, all or portions of the subject innovation may be implemented as a method, apparatus or article of manufacture using standard programming and/or engineering techniques to produce software, firmware, hardware, or any combination thereof to control a computer to implement the disclosed innovation. The term "article of manufacture" as used herein is intended to encompass a computer program accessible from any computer-readable device or media. For example, computer readable media can include but are not limited to magnetic storage devices (e.g., hard disk, floppy disk, magnetic strips . . . ), optical disks (e.g., compact disk (CD), digital versatile disk (DVD). . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Figure 10:
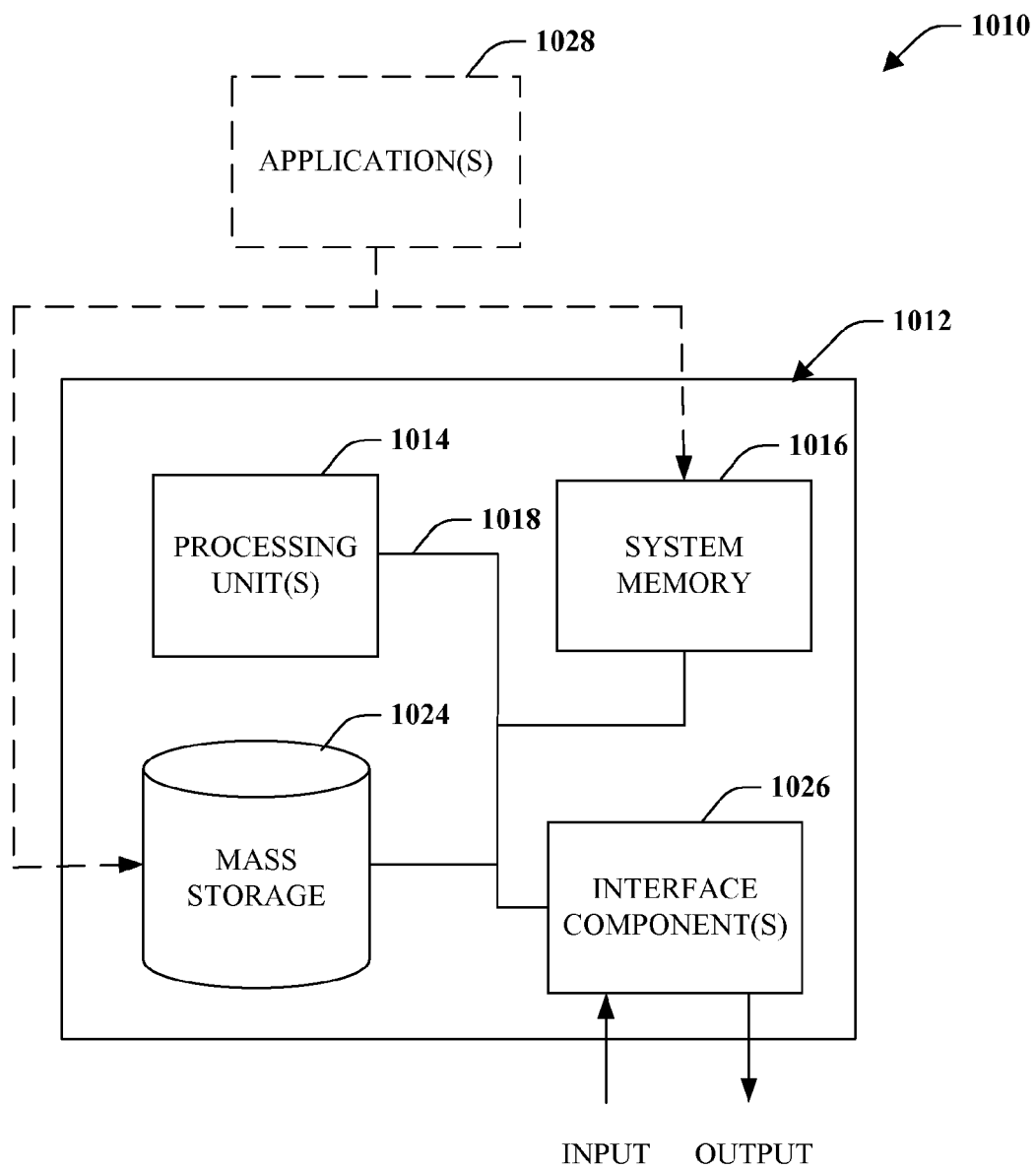
FIG. 10 is a schematic block diagram illustrating a suitable operating environment.
Figure 11:
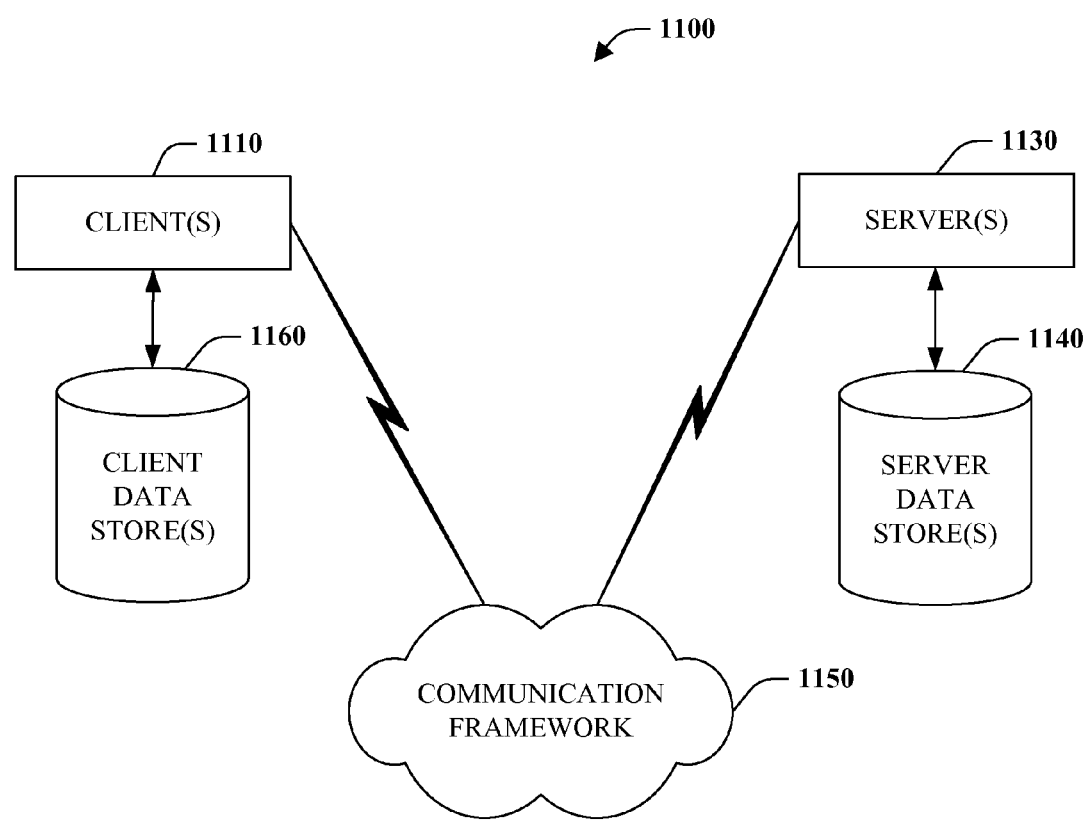
FIG. 11 is a schematic block diagram of a sample-computing environment.

In order to provide a context for the various aspects of the disclosed subject matter, FIGS. 10 and 11 as well as the following discussion are intended to provide a brief, general description of a suitable environment in which the various aspects of the disclosed subject matter may be implemented. While the subject matter has been described above in the general context of computer-executable instructions of a program that runs on one or more computers, those skilled in the art will recognize that the subject innovation also may be implemented in combination with other program modules. Generally, program modules include routines, programs, components, data structures, etc. that perform particular tasks and/or implement particular abstract data types. Moreover, those skilled in the art will appreciate that the systems/methods may be practiced with other computer system configurations, including single-processor, multiprocessor or multi-core processor computer systems, mini-computing devices, mainframe computers, as well as personal computers, hand-held computing devices (e.g., personal digital assistant (PDA), phone, watch . . . ), microprocessor-based or programmable consumer or industrial electronics, and the like. The illustrated aspects may also be practiced in distributed computing environments where tasks are performed by remote processing devices that are linked through a communications network. However, some, if not all aspects of the claimed subject matter can be practiced on stand-alone computers. In a distributed computing environment, program modules may be located in both local and remote memory storage devices.

With reference to FIG. 10, an exemplary environment 1010 for implementing various aspects disclosed herein includes a computer 1012 (e.g., desktop, laptop, server, hand held, programmable consumer or industrial electronics . . . ). The computer 1012 includes a processing unit 1014, a system memory 1016 and a system bus 1018. The system bus 1018 couples system components including, but not limited to, the system memory 1016 to the processing unit 1014. The processing unit 1014 can be any of various available microprocessors. It is to be appreciated that dual microprocessors, multi-core and other multiprocessor architectures can be employed as the processing unit 1014.

The system memory 1016 includes volatile and nonvolatile memory. The basic input/output system (BIOS), containing the basic routines to transfer information between elements within the computer 1012, such as during start-up, is stored in nonvolatile memory. By way of illustration, and not limitation, nonvolatile memory can include read only memory (ROM). Volatile memory includes random access memory (RAM), which can act as external cache memory to facilitate processing.

Computer 1012 also includes removable/non-removable, volatile/non-volatile computer storage media. FIG. 10 illustrates, for example, mass storage 1024. Mass storage 1024 includes, but is not limited to, devices like a magnetic or optical disk drive, floppy disk drive, flash memory or memory stick. In addition, mass storage 1024 can include storage media separately or in combination with other storage media.

FIG. 10 provides software application(s) 1028 that act as an intermediary between users and/or other computers and the basic computer resources described in suitable operating environment 1010. Such software application(s) 1028 include one or both of system and application software. System software can include an operating system, which can be stored on mass storage 1024, that acts to control and allocate resources of the computer system 1012. Application software takes advantage of the management of resources by system software through program modules and data stored on either or both of system memory 1016 and mass storage 1024.

The computer 1012 also includes one or more interface components 1026 that are communicatively coupled to the bus 1018 and facilitate interaction with the computer 1012. By way of example, the interface component 1026 can be a port (e.g., serial, parallel, PCMCIA, USB, FireWire . . . ) or an interface card (e.g., sound, video, network . . . ) or the like. The interface component 1026 can receive input and provide output (wired or wirelessly). For instance, input can be received from devices including but not limited to, a pointing device such as a mouse, trackball, stylus, touch pad, keyboard, microphone, joystick, game pad, satellite dish, scanner, camera, other computer and the like. Output can also be supplied by the computer 1012 to output device(s) via interface component 1026. Output devices can include displays (e.g., CRT, LCD, plasma . . . ), speakers, printers and other computers, among other things.

FIG. 11 is a schematic block diagram of a sample-computing environment 1100 with which the subject innovation can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing the aspects of the subject innovation, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. Here, the client(s) 1110 can correspond to program application components and the server(s) 1130 can provide the functionality of the interface and optionally the storage system, as previously described. The client(s) 1110 are operatively connected to one or more client data store(s) 1160 that can be employed to store information local to the client(s) 1110. Similarly, the server(s) 1130 are operatively connected to one or more server data store(s) 1140 that can be employed to store information local to the servers 1130.

By way of example, a program application component can request personal health information from one or more servers 1130 (and an API stored thereupon or accessible therefrom, for example) via a client 1110. The server(s) 1130 can obtain the desired data from a data store 1140 or a plurality of data stores and apply a transformation, style, and/or schema for example. Subsequently, other program application components can request access to the same or different data from the server(s) 1130.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A computer-implemented system, comprising:
    an application program interface (API), comprising:
        a receiver component configured to receive requests for health-related data from at least one of a plurality of disparate devices including one of a medical health device and a personal fitness tracking device;
        an interpreter component configured to process the requests, and gather at least a subset of requested health-related data from a health integration network, wherein the health integration network comprises a plurality of disparate data stores that respectively store health-related data;
        a transformation component configured to utilize a schema to select a portion of gathered health-related data to return to at least one of the plurality of disparate devices ; and
        an authorization component configured to determine whether a user operating the at least one of the plurality of disparate devices has sufficient credentials for a type of data access specified in the requests;
    an artificial intelligence component configured to create a routine to access and provide the data and related data in response to a single call, the data being stored in a first location and the related data being stored in a second location that is different from the first location;
    a processor; and
    a computer-readable storage medium storing instructions that, when executed by the processor, cause the processor to implement at least one of the receiver component, the interpreter component, the transformation component or the authorization component,
    wherein the medical health device includes one of a blood pressure monitor, a weight scale, a blood sugar level monitor, an intravenous device, a pacemaker, a stethoscope, and an x-ray, and the personal fitness tracking device includes one of a combination heart rate monitor watch, a pedometer, a bicycle speedometer, bicycle odometer, or a stop watch.

2. The computer-implemented system of claim 1, wherein at least a portion of the schema is specified in the requests for health-related data.

3. The computer-implemented system of claim 1, wherein the transformation component is further configured to:
    retrieve style information from the health integration network for a data type of a selected portion of gathered health-related data; and
    apply the style information to the selected portion of the gathered health-related data upon return to the plurality of disparate devices.

4. The computer-implemented system of claim 1, wherein the authorization component is further configured to determine whether the at least one of the plurality of disparate devices requesting the data has sufficient credentials for the type of data access specified in the requests.

5. The computer-implemented system of claim 1, wherein the API further comprises an update component configured to send the data to a connected application in response to at least one of an occurrence of an event or a threshold being exceeded.

6. The computer-implemented system of claim 1, wherein a request is received in extensible markup language (XML) format over a Hypertext Transfer Protocol (HTTP) connection.

7. The computer-implemented system of claim 6, wherein the request received in XML format specifies at least one routine call and at least one parameter for the at least one routine call.

8. The computer-implemented system of claim 1, wherein the plurality of data stores are distributed and at least one of the plurality of data stores stores location information for a record in the plurality of data stores.

9. The computer-implemented system of claim 1, wherein the API further comprises a routine packaging component configured to determine a common set of routines and expose the common set of routines for use by an application.

10. The computer-implemented system of claim 1, wherein the plurality of disparate data stores comprises:
    a directory database configured to obtain information indicative of a location of a patient health reading;
    a dictionary database configured to obtain style and type information for types associated with the patient health reading; and
    a record database configured to obtain the patient health reading.

11. The computer-implemented system of claim 10, wherein the patient health reading is at least one of a blood pressure reading, blood sugar level reading or heart rate.

12. A computer-implemented method of interacting with personal health-related data, the computer-implemented method comprising:
    receiving a request corresponding to a portion of a health-related data record from a first device including one of a medical health device and a personal fitness tracking device and specifying an authentication token for a user operating the first device and from which the request is received;
    requesting data from a health integration network based, at least, on the request;
    applying a schema to the data to prepare a result comprising selected parts of the data; and
    creating a routine to access and provide the data and related data in response to a single call, the data being stored in a first location and the related data being stored in a second location that is different from the first location, wherein the medical health device includes one of a blood pressure monitor, a weight scale, a blood sugar level monitor, an intravenous device, a pacemaker, a stethoscope, and an x-ray, and the personal fitness tracking device includes one of a combination heart rate monitor watch, a pedometer, a bicycle speedometer, bicycle odometer, or a stop watch.

13. The computer-implemented method of claim 12, further comprising sending the result to the first device.

14. The computer-implemented method of claim 13, further comprising receiving information indicative of a time-to-live for the result, wherein the result expires and is not sent to the first device if the time-to-live is exceeded.

15. The computer-implemented method of claim 12, wherein the selected parts are specified in the request for the portion of the health-related data record.

16. The computer-implemented method of claim 12, further comprising receiving a disparate request for the portion of the health-related data record from a second device, wherein the second device operates on a different architecture than the first device.

17. The computer-implemented method of claim 12, wherein the request is to store the portion of the health-related data in the health integration network.

18. The computer-implemented method of claim 17, further comprising sending an event to a second device based, at least, in part, on the request.

19. The computer-implemented method of claim 12, wherein the request is included in an extensible markup language (XML) document.

20. The computer-implemented method of claim 19, wherein the XML document further comprises at least one parameter required by a requested routine.

21. One or more computer storage media having instructions stored thereon that, when executed by a processor, cause operations to be performed comprising:
  receiving and responding to requests for personal health-related data from at least one of a plurality of devices including one of a medical health device and a personal fitness tracking device, wherein the requests specify a signature to be employed for authentication;
  obtaining a subset of stored data relating to the requests; and
  applying at least one schema to the subset of the stored data to return a requested selection of the subset of the stored data,
  wherein the medical health device includes one of a blood pressure monitor, a weight scale, a blood sugar level monitor, an intravenous device, a pacemaker, a stethoscope, and an x-ray, and the personal fitness tracking device includes one of a combination heart rate monitor watch, a pedometer, a bicycle speedometer, bicycle odometer, or a stop watch.

* * * * *